(12) United States Patent
Bauer et al.

(10) Patent No.: US 12,336,895 B2
(45) Date of Patent: Jun. 24, 2025

(54) THIN FLUID ABSORBENT CORE-ABSORBENT PAPER

(71) Applicant: BASF SE, Ludwigshafen am Rhein (DE)

(72) Inventors: Stephan Bauer, Ludwigshafen (DE); Katrin Baumann, Ludwigshafen (DE); Norbert Herfert, Shanghai (CN); Li Guo Duan, Shanghai (CN); Le Li, Shanghai (CN); Xiao Yan Liu, Shanghai (CN); Gao Min Sun, Shanghai (CN)

(73) Assignee: BASF SE, Ludwigshafen am Rhein (DE)

( * ) Notice: Subject to any disclaimer, the term of this patent is extended or adjusted under 35 U.S.C. 154(b) by 902 days.

(21) Appl. No.: 17/048,354

(22) PCT Filed: Apr. 9, 2019

(86) PCT No.: PCT/EP2019/058925
§ 371 (c)(1),
(2) Date: Oct. 16, 2020

(87) PCT Pub. No.: WO2019/201668
PCT Pub. Date: Oct. 24, 2019

(65) Prior Publication Data
US 2021/0169709 A1    Jun. 10, 2021
US 2022/0071818 A9    Mar. 10, 2022

(30) Foreign Application Priority Data

Apr. 20, 2018  (WO) ............... PCT/CN2018/083937
Feb. 11, 2019  (WO) ............... PCT/CN2019/074788

(51) Int. Cl.
*A61F 13/53*   (2006.01)
*A61L 15/24*   (2006.01)
*A61L 15/60*   (2006.01)

(52) U.S. Cl.
CPC .............. *A61F 13/53* (2013.01); *A61L 15/24* (2013.01); *A61L 15/60* (2013.01); *A61F 2013/530591* (2013.01)

(58) Field of Classification Search
CPC .......... A61F 13/53; A61F 2013/530591; A61F 13/537; A61F 2013/530437;
(Continued)

(56) References Cited

U.S. PATENT DOCUMENTS 5,767,213 A * 6/1998 Graham ................. A61L 15/18
528/495
7,163,966 B2  1/2007 Joy et al.
(Continued)

FOREIGN PATENT DOCUMENTS

CN    1889987 A    1/2007
CN    1934170 A    3/2007
(Continued)

OTHER PUBLICATIONS

Fredric L. Buchholz, "Application of Superabsorbent Polymer", Modern Superabsorbent Polymer Technology, ed. Buchholz, et al., 1998, pp. 252-258.
(Continued)

*Primary Examiner* — Susan S Su
*Assistant Examiner* — Katherine-Ph Minh Pham
(74) *Attorney, Agent, or Firm* — Armstrong Teasdale LLP

(57) ABSTRACT

The present disclosure relates to fluid absorbent cores including at least one absorption layer, the layer including at least 80% by weight of water-absorbent polymer particles, 0 to 10% by weight of an adhesive and from 0 to 10% by
(Continued)

weight of fibrous material, wherein the water-absorbent polymer particles within the absorption layer are water-absorbent polymer particles having a vortex of 40 s or less and having a roundness of 0.79 to 0.85 and/or a CRC of 38 g/g to 85 g/g.

15 Claims, 7 Drawing Sheets

(58) Field of Classification Search
CPC ........ A61F 2013/530481; A61F 2013/530708; A61L 15/24; A61L 15/60
See application file for complete search history.

(56) References Cited

U.S. PATENT DOCUMENTS

| | | | |
|---|---|---|---|
| 8,318,306 | B2 | 11/2012 | Tian et al. |
| 8,865,828 | B2 | 10/2014 | Daniel et al. |
| 9,669,386 | B2 | 6/2017 | Wada et al. |
| 10,822,441 | B2 | 11/2020 | Lee et al. |
| 10,881,555 | B2 | 1/2021 | Panayotova et al. |
| 2003/0139715 | A1 | 7/2003 | Dodge, II et al. |
| 2008/0242817 | A1 | 10/2008 | Ducker et al. |
| 2009/0315204 | A1 | 12/2009 | Loesch et al. |
| 2010/0010176 | A1 | 1/2010 | Loesch et al. |
| 2010/0121003 | A1 | 5/2010 | Funk |
| 2012/0232177 | A1* | 9/2012 | Lopez Villanueva .... C08F 2/10 241/24.1 |
| 2012/0288701 | A1 | 11/2012 | Matsushita et al. |
| 2012/0308799 | A1 | 12/2012 | Yamaguchi et al. |
| 2013/0046263 | A1 | 2/2013 | Fukudome et al. |
| 2016/0206772 | A1* | 7/2016 | Schröder ................. A61L 15/60 |
| 2016/0272745 | A1 | 9/2016 | Daniel et al. |
| 2017/0281422 | A1* | 10/2017 | Herfert ................. A61F 13/534 |
| 2017/0281423 | A1* | 10/2017 | Panayotova ............ A61L 15/58 |
| 2017/0281425 | A1 | 10/2017 | Herfert et al. |
| 2017/0312145 | A1* | 11/2017 | Bianchi ............... A61F 13/5376 |

FOREIGN PATENT DOCUMENTS

| | | |
|---|---|---|
| CN | 1934171 A | 3/2007 |
| CN | 101932343 A | 12/2010 |
| CN | 103153455 A | 6/2013 |
| CN | 105237672 A | 1/2016 |
| CN | 107261194 A | 10/2017 |
| CN | 107438637 A | 12/2017 |
| EP | 2550946 A1 | 1/2013 |
| EP | 2565031 A1 | 3/2013 |
| EP | 2668936 A1 | 12/2013 |
| JP | 2006057075 A | 3/2006 |
| WO | 2007031441 A2 | 3/2007 |
| WO | 2008040715 A1 | 4/2008 |
| WO | 2008084031 A2 | 7/2008 |
| WO | 2008086976 A1 | 7/2008 |
| WO | 2011026876 A1 | 3/2011 |
| WO | 2011086842 A1 | 7/2011 |
| WO | 2011086844 A1 | 7/2011 |
| WO | 2011117997 A1 | 9/2011 |
| WO | 2011136087 A1 | 11/2011 |
| WO | 2012048879 A1 | 4/2012 |
| WO | 2012052172 A1 | 4/2012 |
| WO | 2012052173 A1 | 4/2012 |
| WO | 2015028158 A1 | 3/2015 |
| WO | 2015110321 A1 | 7/2015 |
| WO | 2016134905 A1 | 9/2016 |

OTHER PUBLICATIONS

Graham, et al., "Chapter 3—Commercial Processes for the Manufacture of Superabsorbent Polymers", Modern Superabsorbent Polymer Technology, ed. Buchholz, et al., 1998, pp. 71-103.
International Search Report and Written Opinion for corresponding PCT/EP2019/058925 mailed Jun. 4, 2019, 8 pages.

* cited by examiner

THIN FLUID ABSORBENT CORE-ABSORBENT PAPER

CROSS-REFERENCE TO RELATED APPLICATIONS

This application is a U.S. National Phase Application of International Patent Application Number PCT/EP2019/058925, filed on Apr. 9, 2019, which claims the benefit of priority to International Patent Application Number PCT/CN2019/074788, filed Feb. 11, 2019, and to International Patent Application Number PCT/CN2018/083937, filed Apr. 20, 2018, the entire contents of which are hereby incorporated by reference herein.

The present invention relates to fluid absorbent cores (80) comprising at least one absorption layer, the layer comprising at least 80% by weight of water-absorbent polymer particles, 0 to 10% by weight of an adhesive and from 0 to 10% by weight of fibrous material, wherein the water-absorbent polymer particles within the absorption layer are water-absorbent polymer particles H having a vortex of 40 s or less and having a roundness of 0.79 to 0.85 and/or a CRC of 38 g/g to 85 g/g.

The production of fluid-absorbent articles is described in the monograph "Modern Superabsorbent Polymer Technology", F. L. Buchholz and A. T. Graham, Wiley-VCH, 1998, pages 252 to 258.

The current commercially available disposable diapers consist typically of a liquid-pervious topsheet (89), a liquid-impervious backsheet (83), a water-absorbing storage layer (absorbent core) (80) between layers (89) and (83), and an acquisition distribution layer (70) between layers (89) and (80).

Usually the several layers of fluid-absorbent articles fulfill definite functions such as dryness for the upper liquid-pervious layer, vapor permeability without wetting through for the lower liquid-impervious layer, a flexible, vapor permeable and fluid-absorbent core, showing fast absorption rates and being able to retain quantities of body fluids and an optional acquisition-distribution layer between the upper layer and the core, acting as transport and distribution layer of the discharged body fluids.

The preparation of water-absorbing polymer particles is generally described in the monograph "Modern Superabsorbent Polymer Technology", F. L. Buchholz and A. T. Graham, Wiley-VCH, 1998, pages 71 to 103. The water-absorbing polymer particles are also referred to as "fluid-absorbing polymer particles", "superabsorbent polymers" or "superabsorbents".

The preparation of water-absorbent polymer particles by polymerizing droplets of a monomer solution is described, for example, in EP 0 348 180 A1, WO 96/40427 A1, U.S. Pat. No. 5,269,980, WO 2008/009580 A1, WO 2008/052971 A1, WO2011/026876 A1, WO 2011/117263 A1, WO 2014/079694, W2015/028327 and WO 2015/028158.

In the last years, there has been a trend toward very thin disposable diapers. To produce thin disposable diapers, the proportion of cellulose fibers in the water-absorbing storage layer has been lowered or is almost missing.

A core-structure for thin fluid-absorbent products can be formed from absorbent paper. Such structures are for example described in WO2011/086842, EP 2 565 031 A1, EP 2 668 936 A1. But the known thin fluid-absorbent products comprising absorbent paper structures have deficiencies in respect to fluid acquisition, leakage and rewet properties.

To prevent leakage and wet feeling it is preferred to have thicker acquisition-distribution layers so that the time to absorb the body fluid is preferably short. But this contravenes the trend to thinner absorbent articles, as the thickness is also a great issue in respect to absorbent articles especially in respect to noticeability for adult articles and also hindrance, especially for baby diapers and pants.

Another problem is gel blocking as the low amount of fibers or even the absence of fibers within the absorbent core. Upon absorption of liquid the water absorbent polymer particles form a soft gel so that liquid permeation into an internal of the absorbent material is blocked.

Furthermore, the reduction of fibers mal lead to problems with fixing the water-absorbent polymer particles and to reduce the shape retaining ability of the core so that deformation occur before or after liquid absorption.

It is therefore an object of the present invention prevent gel blocking to provide a fluid-absorbent core for fluid-absorbent products with an improved performance even when containing no or only a small amount of fibers (at maximum 10% by weight of fibrous material).

It is also an object of the present invention to provide absorbent cores with improved fluid storage capacity to avoid leakage.

It is furthermore an object of the present invention to provide absorbent cores with improved rewet performance.

It is also an object of the present invention to provide absorbent articles with improved core structures.

It is also an object of the present invention to provide absorbent articles with fast surface dryness (Water pouring Rewet) and long-time dryness, which especially depends on extractables content and CRC of the water absorbent polymer particles. Preferably the extractables (16$h$) content is low as extractables are leaking out of the swollen gel particles over time, thereby reducing the absorbency of the SAP. As a result the rewet increases over time.

It is furthermore an object of the present invention to provide absorbent articles with improved long-time dryness.

The object is achieved by a fluid-absorbent core (80) comprising at least one absorption layer, the layer comprising at least 80% by weight of water-absorbent polymer particles, 0 to 10% by weight of an adhesive and from 0 to 10% by weight of fibrous material, wherein the water-absorbent polymer particles within the absorption layer are water-absorbent polymer particles H having a vortex of 40 s or less and having a roundness of 0.79 to 0.85 and/or a CRC of 38 g/g to 85 g/g. According to the invention it is furthermore preferred that the water-absorbent polymer particles H are surface post-crosslinked. According to the invention it is preferred that the fluid-absorbent core (80) comprises at least two absorption layers, an upper layer (91) and a bottom layer (92), wherein at least the bottom layer (92) comprises water-absorbent polymer particles H.

According to another embodiment of the invention within the fluid absorbent core (80) at least one layer of nonwoven material (94) is sandwiched between the upper layer (91) and the lower layer (92).

In one embodiment of the invention the water-absorbent polymer particles H having a CRC of 38 g/g to 85 g/g, preferably of 40 g/g to 80 g/g, more preferably of 42 g/g to 75 g/g.

According to the invention the water-absorbent polymer particles H having a vortex of 40 s or less, an AUL (21 g cm$^{-2}$) of 22 g/g to 60 g/g, a CRC of 38 g/g to 85 g/g, a VAUL (i=21 g cm-2) of 1000 s or less, a $T_{20}$ of 1000 s or less, a FSC (1 min) of at least 25 g/g/s and a SAP-Rewet (3 min) of 1.5 g or less, According to one embodiment of the invention the Water Pouring Time of the inventive the flu-id absorbent core (80) is 28 s or less and the Water Pouring Rewet the fluid absorbent core (80) is 3.5 g or less measured according to the method "Water pouring test" disclosed herein. According to the invention the fluid absorbent core (80) having a Liquid Diffusion Length of at least 245 mm, a total strike-thru time of 45 s or less and a Total Rewet of 40 g or less measured according to the method "Strike-thru/Rewet" disclosed in the description.

The inventive fluid-absorbent core may be part of absorbent articles.

According to the invention an inventive absorbent article, comprising
an upper liquid-pervious sheet (89),
a lower liquid-impervious sheet (83),
a fluid absorbent core (80) according to any embodiment of the inventive absorbent core;
an optional acquisition distribution layer (70) between the upper liquid-pervious sheet (89) and the fluid-absorbent core (80),
other optional components.

DETAILED DESCRIPTION OF THE INVENTION

Definitions

As used herein, the term "fluid-absorbent article" refers to any three-dimensional solid material being able to acquire and store fluids discharged from the body. Preferred fluid-absorbent articles are disposable fluid-absorbent articles that are designed to be worn in contact with the body of a user such as disposable fluid-absorbent pantyliners, sanitary napkins, catamenials, incontinence inserts/pads, diapers, training pant diapers, breast pads, interlabial inserts/pads or other articles useful for absorbing body fluids.

As used herein, the term "fluid-absorbent composition" refers to a component of the fluid-absorbent article which is primarily responsible for the fluid handling of the fluid-absorbent article including acquisition, transport, distribution and storage of body fluids.

Figure 4:
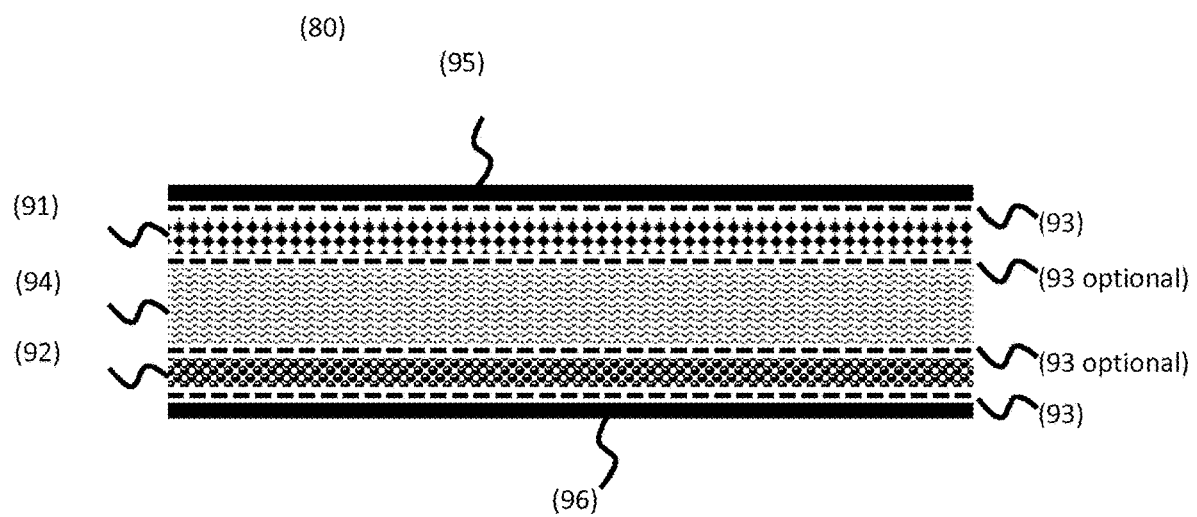
FIG. 4 illustrates a schematic view of absorbent core (80)

As used herein, the term "fluid-absorbent core", "absorbent core" or "absorbent paper" refers to a fluid-absorbent composition comprising at least one, preferably at least two layers including an upper layer and a lower layer of water-absorbent polymer particles and optionally fibrous material (at maximum 10% by weight of fibrous material); nonwoven material and tissue material and optionally adhesive. The fluid-absorbent core is primarily responsible for the fluid handling of the fluid-absorbent article including acquisition, transport, distribution and storage of body fluids. A fluid absorbent core according to the invention is shown in FIG. 4.

As used herein, the term "layer" refers to a fluid-absorbent composition whose primary dimension is along its length and width. Thus a layer usually comprises water-absorbent polymer particles and optionally fibrous material, a layer can comprise laminates, composites, combinations of several sheets or webs of different materials.

As used herein the term "x-dimension" refers to the length, and the term "y-dimension" refers to the width of the fluid-absorbent composition, layer, core or article. Generally, the term "x-y-dimension" refers to the plane, orthogonal to the height or thickness of the fluid-absorbent composition, layer, core or article.

As used herein the term "z-dimension" refers to the dimension orthogonal to the length and width of the fluid absorbent composition, layer, core or article. Generally, the term "z-dimension" refers to the height of the fluid-absorbent composition, layer, core or article.

As used herein, the term "basis weight" indicates the weight of the fluid-absorbent core or any tissue per square meter and does not include the chassis of the fluid-absorbent article. The basis weight is determined at least at two different regions of the fluid-absorbent core or any tissue respectively and is taken as the average of the at least two results.

Further, it should be understood, that the term "upper" refers to fluid-absorbent composition which are nearer to the wearer of the fluid-absorbent article. Generally, the topsheet in an absorbent article is the nearest composition to the wearer of the fluid-absorbent article, hereinafter described as "upper liquid-pervious layer". Contrarily, the term "lower" refers to fluid-absorbent compositions which are away from the wearer of the fluid-absorbent article. Generally, the backsheet is the component which is furthermost away from the wearer of the fluid-absorbent article, hereinafter described as "lower liquid-impervious layer".

As used herein, the term "liquid-pervious" refers to a substrate, layer or a laminate thus permitting liquids, i.e. body fluids such as urine, menses and/or vaginal fluids to readily penetrate through its thick-ness.

As used herein, the term "liquid-impervious" refers to a substrate, layer or a laminate that does not allow body fluids to pass through in a direction generally perpendicular to the plane of the layer at the point of liquid contact under ordinary use conditions.

As used herein, the term "chassis" refers to fluid-absorbent material comprising the upper liquid-pervious layer and the lower liquid-impervious layer, elastics (and closure systems for the absorbent article.

As used herein, the term "hydrophilic" refers to the wettability of fibers by water deposited on these fibers. The term "hydrophilic" is defined by the contact angle and surface tension of the body fluids. According to the definition of Robert F. Gould in the 1964 American Chemical Society publication "Contact angle, wettability and adhesion", a fiber is referred to as hydrophilic, when the contact angle between the liquid and the fiber, especially the fiber sur-face, is less than 90° or when the liquid tends to spread spontaneously on the same surface.

Contrarily, term "hydrophobic" refers to fibers showing a contact angle of greater than 90° or no spontaneously spreading of the liquid across the surface of the fiber.

As used herein, the term "body fluids" refers to any fluid produced and discharged by human or animal body, such as urine, menstrual fluids, faeces, vaginal secretions and the like.

As used herein, the term "breathable" refers to a substrate, layer, film or a laminate that allows vapour to escape from the fluid-absorbent article, while still preventing fluids from leakage. Breathable substrates, layers, films or laminates may be porous polymeric films, nonwoven laminates from spunbond and melt-blown layers, laminates from porous polymeric films and nonwovens.

As used herein, the term "longitudinal" refers to a direction running perpendicular from a waist edge to an opposing waist edge of the fluid-absorbent article.

Water-Absorbent Polymer Particles

The water-absorbent polymer particles according to the invention are prepared by a process, comprising the steps forming water-absorbent polymer particles by polymerizing a monomer solution, comprising
- a) at least one ethylenically unsaturated monomer which bears acid groups and may be at least partly neutralized,
- b) one or more crosslinker,
- c) at least one initiator,
- d) water,
in a surrounding heated gas phase, coating the water-absorbent polymer particles with at least one surface-postcrosslinker and thermal surface-postcrosslinking of the coated water-absorbent polymer particles The water-absorbent polymer particles are typically insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid having a concentration of diacrylic acid from 0 to 2% by weight, more preferably 0.0001 to 1% by weight, most preferably from 0.0002 to 0.5% by weight.

The acid groups of the monomers a) are typically partly neutralized, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogen carbonates, and mixtures thereof.

Acrylic acid typically comprises polymerization inhibitors, preferably hydroquinone monoethers, as storage stabilizers.

Suitable crosslinkers b) are compounds having at least two groups suitable for crosslinking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b). The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and tri-acrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or crosslinker mixtures, as described, for example, in DE 195 43 368 A1, DE 196 46 484 A1, WO 90/15830 A1 and WO 2002/32962 A2.

The amount of crosslinker b) is preferably from 0.0001 to 0.6% by weight, more preferably from 0.0015 to 0.2% by weight, most preferably from 0.01 to 0.06% by weight, based in each case on monomer a). On increasing the amount of crosslinker b) the centrifuge retention capacity (CRC) decreases and the absorption under a pressure of 21.0 g/cm$^2$ (AUL) passes through a maximum.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion. The initiators c) should be water-soluble.

Particularly preferred initiators c) are azo initiators such as 2,2"-azobis[2-(2-imidazolin-2-yl)propane] dihydrochloride, 2,2"-azobis[2-(5-methyl-2-imidazolin-2-yl)propane] dihydrochloride, 2,2"-azobis(2-amidinopropane)dihydrochloride, 4,4"-azobis(4-cyanopentanoic acid), 4,4"-azobis (4-cyanopentanoic acid) sodium salt, 2,2'-azobis[2-methyl-N-(2-hydroxyethyl)-propionamide and 2,2"-azobis[2-(5-methyl-2-imidazolin-2-yl)propane] dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Bruggolite® FF6 and Bruggolite® FF7 (Brüggemann Chemicals; Heilbronn; Germany). Of course it is also possible within the scope of the present invention to use the purified salts or acids of 2-hydroxy-2-sulfinatoacetic acid and 2-hydroxy-2-sulfonatoacetic acid—the latter being available as sodium salt under the trade name Blancolen® HP (Brüggemann Chemicals; Heilbronn; Germany).

In a preferred embodiment of the present invention a combination of at least one persulfate c1) and at least one azo initiator c2) is used as initiator c).

The amount of persulfate c1) to be used is preferably from 0.01 to 0.25% by weight, more preferably from 0.05 to 0.2% by weight, most preferably from 0.1 to 0.15% by weight, each based on monomer a). If the amount of persulfate is too low, a sufficient low level of residual monomers cannot be achieved. If the amount of persulfate is too high, the water-absorbent polymer particles do not have a sufficient whiteness and may suffer degradation upon heating.

The amount of azo initiator c2) to be used is preferably from 0.1 to 2% by weight, more preferably from 0.15 to 1% by weight, most preferably from 0.2 to 0.5% by weight, each based on monomer a). If the amount of azo initiator is too low, a high centrifuge retention capacity (CRC) cannot be achieved. If the amount of azo initiator is too high, the process becomes too expensive.

In a more preferred embodiment of the present invention a combination of at least one persulfate c1), a reducing component, and at least one azo initiator c2) is used as initiator c).

The amount of reducing component to be used is preferably from 0.0002 to 1% by weight, more preferably from 0.0001 to 0.8% by weight, more preferably from 0.0005 to 0.6% by weight, most preferably from 0.001 to 0.4% by weight, each based on monomer a).

For optimal action, the preferred polymerization inhibitors require dissolved oxygen. Therefore, the monomer solution can be freed of dissolved oxygen before the polymerization by inertization, i.e. flowing through with an inert gas, preferably nitrogen. It is also possible to reduce the concentration of dissolved oxygen by adding a reducing agent. The oxygen content of the monomer solution is preferably lowered before the polymerization to less than 1 ppm by weight, more preferably to less than 0.5 ppm by weight.

The water content of the monomer solution is preferably less than 65% by weight, preferentially less than 62% by weight, more preferably less than 60% by weight, most preferably less than 58% by weight.

The monomer solution has, at 20° C., a dynamic viscosity of preferably from 0.002 to 0.02 Pas, more preferably from 0.004 to 0.015 Pas, most preferably from 0.005 to 0.01 Pas. The mean droplet diameter in the droplet generation rises with rising dynamic viscosity.

The monomer solution has, at 20° C., a density of preferably from 1 to 1.3 g/cm$^3$, more preferably from 1.05 to 1.25 g/cm$^3$, most preferably from 1.1 to 1.2 g/cm$^3$.

The monomer solution has, at 20° C., a surface tension of from 0.02 to 0.06 N/m, more preferably from 0.03 to 0.05 N/m, most preferably from 0.035 to 0.045 N/m. The mean droplet diameter in the droplet generation rises with rising surface tension.

Additives for colour stability and additives for reducing residual monomers can also be added to the monomer solution. The preferred amount of the additive for colour stability in the monomer solution is at least of 0.001%, preferably from 0.005% to 5% by weight, more preferably from 0.01 to 3% by weight, most preferably from 0.02 to 2% by weight, each based on monomer a).

The water-absorbent polymer particles are produced by polymerizing droplets of the monomer in a surrounding heated gas phase, for example using a system described in WO 2008/040715 A2, WO 2008/052971 A1, WO 2008/069639 A1 and WO 2008/086976 A1, or in a surrounding hydrophobic solvent, for example using a system described in WO 2008/068208 A1 and WO 2008/084031 A1.

The droplets are preferably generated by means of a droplet plate. A droplet plate is a plate having a multitude of bores, the liquid entering the bores from the top. The droplet plate or the liquid can be oscillated, which generates a chain of ideally monodisperse droplets at each bore on the underside of the droplet plate. In a preferred embodiment, the droplet plate is not agitated.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. In a preferred embodiment of the present invention the pressure drop is from 4 to 5 bar. The Reynolds number based on the throughput per bore and the bore diameter is preferably less than 2000, preferentially less than 1600, more preferably less than 1400 and most preferably less than 1200.

The underside of the droplet plate has at least in part a contact angle preferably of at least 60°, more preferably at least 75° and most preferably at least 90° with regard to water.

The contact angle is a measure of the wetting behavior of a liquid, in particular water, with regard to a surface, and can be determined using conventional methods, for example in accordance with ASTM D 5725. A low contact angle denotes good wetting, and a high contact angle denotes poor wetting.

It is also possible for the droplet plate to consist of a material having a lower contact angle with regard to water, for example a steel having the German construction material code number of 1.4571, and be coated with a material having a larger contact angle with regard to water.

It is the poor wettability of the droplet plate that leads to the production of monodisperse droplets of narrow droplet size distribution.

The droplet plate has preferably at least 5, more preferably at least 25, most preferably at least 50 and preferably up to 2000, more preferably up to 1500 bores, most preferably up to 1000. The diameter of the bores is adjusted to the desired droplet size.

The spacing of the bores is usually from 2 to 50 mm, preferably from 3 to 40 mm, more preferably from 4 to 30 mm, most preferably from 5 to 25 mm, preferentially 4 to 9 mm. Smaller spacings of the bores may cause agglomeration of the polymerizing droplets.

The diameter of the bores size area is 1900 to 22300 µm$^2$, more preferably from 7800 to 20100 µm$^2$, most preferably from 11300 to 17700 µm$^2$. Circular bores are preferred with a bore size from 50 to 170 µm, more preferably from 100 to 160 µm, most preferably from 120 to 150 µm.

For optimizing the average particle diameter, droplet plates with different bore diameters can be used. The variation can be done by different bores on one plate or by using different plates, where each plate has a different bore diameter. The average particle size distribution can be monomodal, bimodal or multimodal. Most preferably it is monomodal or bimodal.

The temperature of the monomer solution as it passes through the bore is preferably from 5 to 80° C., more preferably from 10 to 70° C., most preferably from 30 to 60° C.

A carrier gas flows through the reaction zone. The carrier gas may be conducted through the reaction zone in cocurrent to the free-falling droplets of the monomer solution, i.e. from the top downward. After one pass, the gas is preferably recycled at least partly, preferably to an extent of at least 50%, more preferably to an extent of at least 75%, into the reaction zone as cycle gas. Typically, a portion of the carrier gas is discharged after each pass, preferably up to 10%, more preferably up to 3% and most preferably up to 1%.

The oxygen content of the carrier gas is preferably from 0.1 to 25% by volume, more preferably from 1 to 10% by volume, most preferably from 2 to 7% by weight. In the scope of the present invention it is also possible to use a carrier gas which is free of oxygen.

As well as oxygen, the carrier gas preferably comprises nitrogen. The nitrogen content of the gas is preferably at least 80% by volume, more preferably at least 90% by volume, most preferably at least 95% by volume. Other possible carrier gases may be selected from carbon dioxide, argon, xenon, krypton, neon, helium, sulfurhexafluoride. Any mixture of carrier gases may be used. It is also possible to use air as carrier gas. The carrier gas may also become loaded with water and/or acrylic acid vapors.

The gas velocity is preferably adjusted such that the flow in the reaction zone (5) is directed, for example no convection currents opposed to the general flow direction are present, and is preferably from 0.1 to 2.5 m/s, more preferably from 0.3 to 1.5 m/s, even more preferably from 0.5 to 1.2 m/s, most preferably from 0.7 to 0.9 m/s.

The gas entrance temperature, i.e. the temperature with which the gas enters the reaction zone, is preferably from 160 to 200° C., more preferably from 165 to 195° C., even more preferably from 170 to 190° C., most preferably from 175 to 185° C.

The steam content of the gas that enters the reaction zone is preferably from 0.01 to 0.15 kg per kg dry gas, more from 0.02 to 0.12 kg per kg dry gas, most from 0.03 to 0.10 kg per kg dry gas.

The gas entrance temperature is controlled in such a way that the gas exit temperature, i.e. the temperature with which the gas leaves the reaction zone, is less than 150° C., preferably from 90 to 140° C., more preferably from 100 to 130° C., even more preferably from 105 to 125° C., most preferably from 110 to 120° C.

Most preferably the gas entrance temperature is from 175 to 185° C. and the temperature with which the gas leaves the reaction zone preferably from 110 to 120° C.

The water-absorbent polymer particles can be divided into three categories: water-absorbent polymer particles of Type 1 are particles with one cavity, water-absorbent polymer particles of Type 2 are particles with more than one cavity, and water-absorbent polymer particles of Type 3 are solid particles with no visible cavity.

The morphology of the water-absorbent polymer particles can be controlled by the reaction conditions during polymerization. Water-absorbent polymer particles having a high amount of particles with one cavity (Type 1) can be prepared by using low gas velocities and high gas exit temperatures. Water-absorbent polymer particles having a high amount of particles with more than one cavity (Type 2) can be prepared by using high gas velocities and low gas exit temperatures.

Water-absorbent polymer particles having more than one cavity (Type 2) show an improved mechanical stability.

The reaction can be carried out under elevated pressure or under reduced pressure, preferably from 1 to 100 mbar below ambient pressure, more preferably from 1.5 to 50 mbar below ambient pressure, most preferably from 2 to 10 mbar below ambient pressure.

The reaction off-gas, i.e. the gas leaving the reaction zone, may be cooled in a heat exchanger. This condenses water and unconverted monomer a). The reaction off-gas can then be reheated at least partly and recycled into the reaction zone as cycle gas. A portion of the reaction off-gas can be discharged and replaced by fresh gas, in which case water and unconverted monomers a) present in the reaction off-gas can be removed and recycled.

Particular preference is given to a thermally integrated system, i.e. a portion of the waste heat in the cooling of the off-gas is used to heat the cycle gas.

The reactors can be trace-heated. In this case, the trace heating is adjusted such that the wall temperature is at least 5° C. above the internal surface temperature and condensation on the surfaces is reliably prevented.

The formed water-absorbent polymer particles are thermal posttreated in a fluidized bed. In a preferred embodiment of the present invention an internal fluidized bed is used. An internal fluidized bed means that the product of the dropletization polymerization is accumulated in a fluidized bed below the reaction zone.

The residual monomers can be removed during the thermal posttreatment. What is important here is that the water-absorbent polymer particles are not too dry. In the case of excessively dry particles, the residual monomers decrease only insignificantly. A too high water content increases the caking tendency of the water-absorbent polymer particles.

In the fluidized state, the kinetic energy of the polymer particles is greater than the cohesion or adhesion potential between the polymer particles.

The fluidized state can be achieved by a fluidized bed. In this bed, there is upward flow toward the water-absorbing polymer particles, so that the particles form a fluidized bed. The height of the fluidized bed is adjusted by gas rate and gas velocity, i.e. via the pressure drop of the fluidized bed (kinetic energy of the gas).

The velocity of the gas stream in the fluidized bed is preferably from 0.3 to 2.5 m/s, more preferably from 0.4 to 2.0 m/s, most preferably from 0.5 to 1.5 m/s.

The pressure drop over the bottom of the internal fluidized bed is preferably from 1 to 100 mbar, more preferably from 3 to 50 mbar, most preferably from 5 to 25 mbar.

The moisture content of the water-absorbent polymer particles at the end of the thermal post-treatment is preferably from 1 to 20% by weight, more preferably from 2 to 15% by weight, even more preferably from 3 to 12% by weight, most preferably 6 to 9% by weight.

The temperature of the water-absorbent polymer particles during the thermal posttreatment is from 20 to 140° C., preferably from 40 to 110° C., more preferably from 50 to 105° C., most preferably from 60 to 100° C.

The average residence time in the internal fluidized bed is from 10 to 300 minutes, preferably from 60 to 270 minutes, more preferably from 40 to 250 minutes, most preferably from 120 to 240 minutes.

In one embodiment of the present invention the thermal posttreatment is completely or at least partially done in an external fluidized bed. The operating conditions of the external fluidized bed are within the scope for the internal fluidized bed as described above.

The level of residual monomers can be further reduced by an additional thermal posttreatment in a mixer with rotating mixing tools as described in WO 2011/117215 A1.

The morphology of the water-absorbent polymer particles can also be controlled by the reaction conditions during thermal posttreatment. Water-absorbent polymer particles having a high amount of particles with one cavity (Type 1) can be prepared by using high product temperatures and short residence times. Water-absorbent polymer particles having a high amount of particles with more than one cavity (Type 2) can be prepared by using low product temperatures and long residence times.

To further improve the properties, the polymer particles may subsequently be thermally surface post-crosslinked.

Surface-postcrosslinkers are compounds which comprise groups which can form at least two covalent bonds with the carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols as described in DE 33 14 019 A1, DE 35 23 617 A1 and EP 0 450 922 A2, or β-hydroxyalkylamides, as described in DE 102 04 938 A1 and U.S. Pat. No. 6,239,230. Also ethyleneoxide, aziridine, glycidol, oxetane and its derivatives may be used.

Polyvinylamine, polyamidoamines and polyvinylalcohole are examples of multifunctional polymeric surface-postcrosslinkers.

In addition, DE 40 20 780 C1 describes alkylene carbonates, DE 198 07 502 A1 describes 1,3-oxazolidin-2-one and its derivatives such as 2-hydroxyethyl-1,3-oxazolidin-2-one, DE 198 07 992 C1 describes bis- and poly-1,3-oxazolidin-2-ones, EP 0 999 238 A1 describes bis- and poly-1,3-oxazolidines, DE 198 54 573 A1 describes 2-oxotetrahydro-1,3-oxazine and its derivatives, DE 198 54 574 A1 describes N-acyl-1,3-oxazolidin-2-ones, DE 102 04 937 A1 describes cyclic ureas, DE 103 34 584 A1 describes bicyclic amide acetals, EP 1 199 327 A2 describes oxetanes and cyclic ureas, and WO 2003/31482 A1 describes morpholine-2,3-dione and its derivatives, as suitable surface-postcrosslinkers.

In addition, it is also possible to use surface-postcrosslinkers which comprise additional polymerizable ethylenically unsaturated groups, as described in DE 37 13 601 A1.

In a preferred embodiment of the present invention the at least one surface-postcrosslinker is selected from alkylene carbonates, 1,3-oxazolidin-2-ones, bis- and poly-1,3-oxazolidin-2-ones, bis- and poly-1,3-oxazolidines, 2-oxotetrahydro-1,3-oxazines, N-acyl-1,3-oxazolidin-2-ones, N-hydroxyethyl-1,3-oxazolidin-2-ones, cyclic ureas, bicyclic amide acetals, oxetanes, and morpholine-2,3-diones.

It is also possible to use any suitable mixture of surface-postcrosslinkers. It is particularly favor-able to use mixtures of 1,3-dioxolan-2-on (ethylene carbonate) and 1,3-oxazolidin-2-ones.

In a more preferred embodiment of the present invention at least one alkylene carbonate is used as surface-postcrosslinker. Suitable alkylene carbonates are 1,3-dioxolan-2-on (ethylene carbonate), 4-methyl-1,3-dioxolan-2-on (propylene carbonate), 4,5-dimethyl-1,3-dioxolan-2-on, most preferably 1,3-dioxolan-2-on (ethylene carbonate).

In a most preferred embodiment of the present invention a mixture of ethylene carbonate and diglycidyl ethers, for example mono-, di- and polyethylene glycol diglycidyl ether, is used as surface-postcrosslinker.

The amount of surface-postcrosslinker is preferably from 0.01 to 10% by weight, more preferably from 0.5 to 7.5% by weight, most preferably from 1 to 5% by weight, based in each case on the polymer.

The content of residual monomers in the water-absorbent polymer particles prior to the coating with the surface-postcrosslinker is in the range from 0.03 to 15% by weight, preferably from 0.05 to 12% by weight, more preferably from 0.1 to 10% by weight, even more preferably from 0.15 to 7.5% by weight, most preferably from 0.2 to 5% by weight, even most preferably from 0.25 to 2.5% by weight.

The moisture content of the water-absorbent polymer particles prior to the thermal surface-postcrosslinking is preferably from 1 to 20% by weight, more preferably from 2 to 15% by weight, most preferably from 3 to 10% by weight.

In a preferred embodiment of the present invention, polyvalent cations are applied to the particle surface in addition to the surface-postcrosslinkers before, during or after the thermal surface-postcrosslinking.

The polyvalent cations usable in the process according to the invention are, for example, trivalent cations such as the cations of aluminum, iron, chromium, rare earths and manganese, tetravalent cations such as the cations of titanium and zirconium, and mixtures thereof. Possible counterions are chloride, bromide, sulfate, hydrogensulfate, carbonate, hydrogencarbonate, nitrate, hydroxide, phosphate, hydrogenphosphate, dihydrogenphosphate and carboxylate, such as acetate, glycolate, tartrate, formiate, propionate, 3-hydroxypropionate, lactamide and lactate, and mixtures thereof. Aluminum sulfate, aluminum acetate, and aluminum lactate are preferred. A single metal salt can be used as well as any mixture of the metal salts and/or the polyamines above.

Preferred polyvalent cations and corresponding anions are disclosed in WO 2012/045705 A1 and are expressly incorporated herein by reference. Preferred polyvinylamines are disclosed in WO 2004/024816 A1 and are expressly incorporated herein by reference.

The amount of polyvalent cation used is, for example, from 0.001 to 1.5% by weight, preferably from 0.005 to 1% by weight, more preferably from 0.02 to 0.8% by weight, based in each case on the polymer.

The addition of the polyvalent metal cation can take place prior, after, or cocurrently with the surface-postcrosslinking. Depending on the formulation and operating conditions employed it is possible to obtain a homogeneous surface coating and distribution of the polyvalent cation or an inhomogenous typically spotty coating. Both types of coatings and any mixes between them are useful within the scope of the present invention.

The surface-postcrosslinking is typically performed in such a way that a solution of the surface-postcrosslinker is sprayed onto the hydrogel or the dry polymer particles. After the spraying, the polymer particles coated with the surface-postcrosslinker are dried thermally and cooled.

The spraying of a solution of the surface-postcrosslinker is preferably performed in mixers with moving mixing tools, such as screw mixers, disk mixers and paddle mixers. Suitable mixers are, for example, vertical Schugi Flexomix® mixers (Hosokawa Micron BV; Doetinchem; the Netherlands), Turbolizers® mixers (Hosokawa Micron BV; Doetinchem; the Netherlands), horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Ruberg continuous flow mixers and horizontal Pflugschar® plowshare mixers are preferred. The surface-postcrosslinker solution can also be sprayed into a fluidized bed.

The solution of the surface-postcrosslinker can also be sprayed on the water-absorbent polymer particles during the thermal posttreatment. In such case the surface-postcrosslinker can be added as one portion or in several portions along the axis of thermal posttreatment mixer. In one embodiment it is preferred to add the surface-postcrosslinker at the end of the thermal post-treatment step. As a particular advantage of adding the solution of the surface-postcrosslinker during the thermal posttreatment step it may be possible to eliminate or reduce the technical effort for a separate surface-postcrosslinker addition mixer.

The surface-postcrosslinkers are typically used as an aqueous solution. The addition of nonaqueous solvent can be used to adjust the penetration depth of the surface-postcrosslinker into the polymer particles.

The thermal surface-postcrosslinking is preferably carried out in contact dryers, more preferably paddle dryers, most preferably disk dryers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany), Holo-Flite® dryers (Metso Minerals Industries Inc.; Danville; U.S.A.) and Nara paddle driers (NARA Machinery Europe; Frechen; Germany). Nara paddle driers and, in the case of low process temperatures (<160° C.) for example, when using polyfunctional epoxides, Holo-Flite® dryers are preferred. Moreover, it is also possible to use fluidized bed dryers. In the latter case the reaction times may be shorter compared to other embodiments.

When a horizontal dryer is used then it is often advantageous to set the dryer up with an inclined angle of a few degrees vs. the earth surface in order to impart proper product flow through the dryer. The angle can be fixed or may be adjustable and is typically between 0 to 10 degrees, preferably 1 to 6 degrees, most preferably 2 to 4 degrees.

In one embodiment of the present invention a contact dryer is used that has two different heating zones in one apparatus. For example Nara paddle driers are available with just one heated zone or alternatively with two heated zones. The advantage of using a two or more heated zone dryer is that different phases of the thermal post-treatment and/or of the post-surface-crosslinking can be combined.

In one preferred embodiment of the present invention a contact dryer with a hot first heating zone is used which is followed by a temperature holding zone in the same dryer. This set up allows a quick rise of the product temperature and evaporation of surplus liquid in the first heating zone, whereas the rest of the dryer is just holding the product temperature stable to complete the reaction.

In another preferred embodiment of the present invention a contact dryer with a warm first heating zone is used which is then followed by a hot heating zone. In the first warm zone the thermal post-treatment is affected or completed whereas the surface-postcrosslinking takes place in the subsequential hot zone.

In a typical embodiment a paddle heater with just one temperature zone is employed.

A person skilled in the art will depending on the desired finished product properties and the available base polymer qualities from the polymerization step choose any one of these set ups.

The thermal surface-postcrosslinking can be effected in the mixer itself, by heating the jacket, blowing in warm air or steam. Equally suitable is a downstream dryer, for example a shelf dryer, a rotary tube oven or a heatable screw. It is particularly advantageous to mix and dry in a fluidized bed dryer.

Preferred thermal surface-postcrosslinking temperatures are in the range from 100 to 180° C., preferably from 120 to 170° C., more preferably from 130 to 165° C., most preferably from 140 to 160° C. The preferred residence time at this temperature in the reaction mixer or dryer is preferably at least 5 minutes, more preferably at least 20 minutes, most preferably at least 40 minutes, and typically at most 120 minutes.

It is preferable to cool the polymer particles after thermal surface-postcrosslinking. The cooling is preferably carried out in contact coolers, more preferably paddle coolers, most preferably disk coolers. Suitable coolers are, for example, Hosokawa Bepex® horizontal paddle coolers (Hosokawa Micron GmbH; Leingarten; Germany), Hosokawa Bepex® disk coolers (Hosokawa Micron GmbH; Leingarten; Germany), Holo-Flite® coolers (Metso Minerals Industries Inc.; Danville; U.S.A.) and Nara paddle coolers (NARA Machinery Europe; Frechen; Germany). Moreover, it is also possible to use fluidized bed coolers.

In the cooler the polymer particles are cooled to temperatures of in the range from 20 to 150° C., preferably from 40 to 120° C., more preferably from 60 to 100° C., most preferably from 70 to 90° C. Cooling using warm water is preferred, especially when contact coolers are used.

To improve the properties, the water-absorbent polymer particles can be coated and/or optionally moistened as e.g. described in WO2016124905. The internal fluidized bed, the external fluidized bed and/or the external mixer used for the thermal posttreatment and/or a separate coater (mixer) can be used for coating of the water-absorbent polymer particles. Further, the cooler and/or a separate coater (mixer) can be used for coating/moistening of the surface-post-crosslinked water-absorbent polymer particles. The water-absorbent polymer particles can further be selectively agglomerated. The agglomeration can take place after any process step after the polymerization, The water-absorbent polymer particles can further be moistened with water and/or steam to improve the damage stability their tendency to static charging. The moisture content is preferably at least 1% by weight, more preferably from 2 to 20% by weight, most preferably 5 to 12% by weight, based on the water-absorbent polymer particles.

Suitable coatings for controlling the acquisition behavior and improving the permeability (SFC or GBP) are, for example, inorganic inert substances, such as water-insoluble metal salts, organic polymers, cationic polymers, anionic polymers and polyvalent metal cations. Suitable coatings for improving the color stability are, for example reducing agents, chelating agents and anti-oxidants. Suitable coatings for dust binding are, for example, polyols. Suitable coatings against the undesired caking tendency of the polymer particles are, for example, fumed silica, such as Aerosil® 200, and surfactants, such as Span® 20. Preferred coatings are aluminium dihydroxy monoacetate, aluminium sulfate, aluminium lactate, aluminium 3-hydroxypropionate, zirconium acetate, citric acid or its water soluble salts, di- and monophosphoric acid or their water soluble salts, Blancolen®, Bruggolite® FF7, Cublen®, Plantacare® 818 UP and Span® 20.

Figure 6:
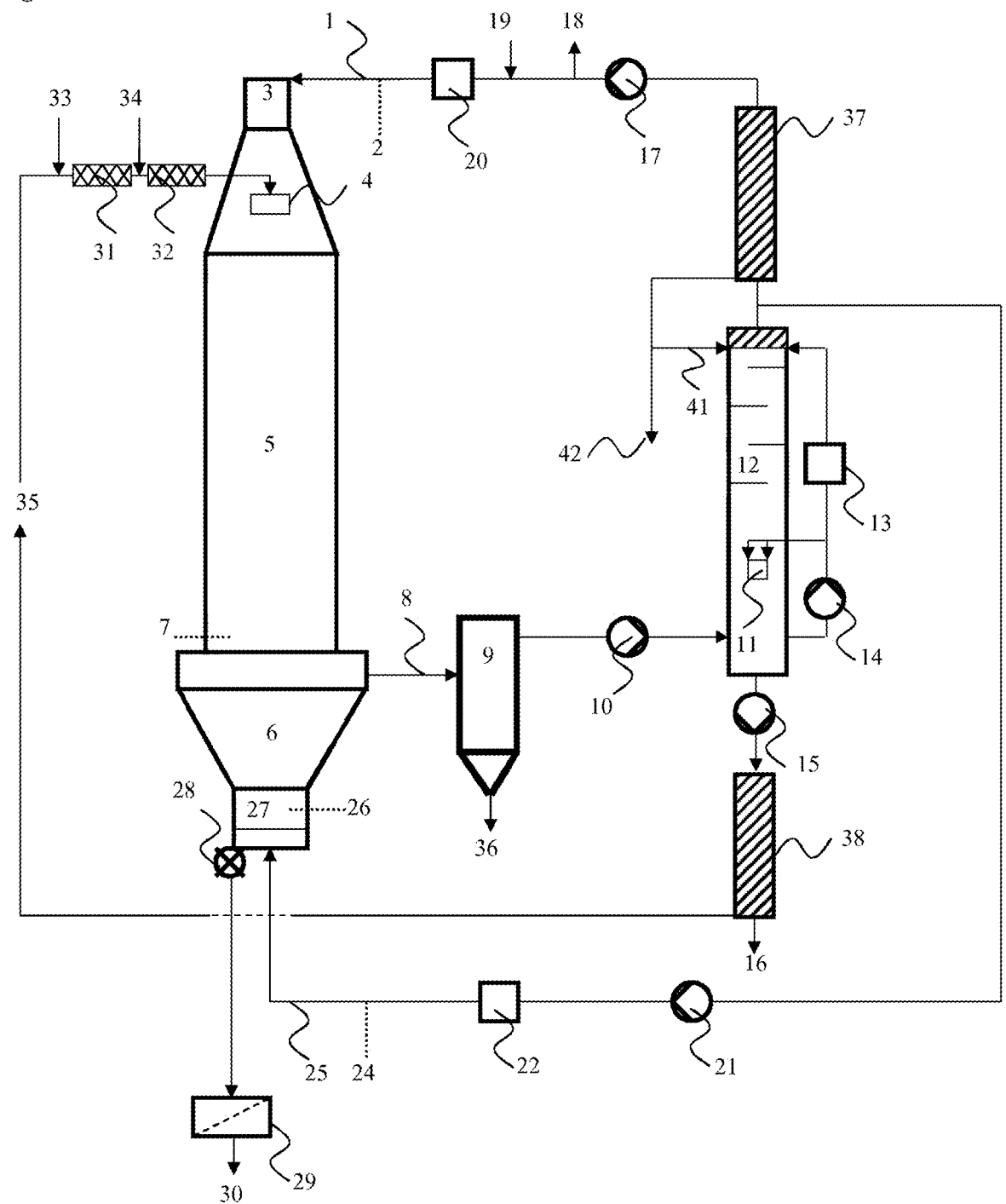
FIG. 6 illustrates how the drying gas is fed via a gas distributor (3) at the top of the spray dryer.

Preferred embodiments are described in the following:

The drying gas is fed via a gas distributor (3) at the top of the spray dryer as shown in FIG. 6. The drying gas is partly recycled (drying gas loop) via a baghouse filter or cyclone unit (9) and a condenser column (12). The pressure inside the spray dryer is below ambient pressure.

Figure 7:
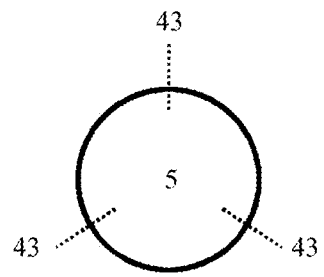
FIG. 7 illustrates how the temperature of the gas leaving the reaction zone (5) was measured at three points around the circumference at the end of the cylindrical part of the spray dryer.

The spray dryer outlet temperature is preferably measured at three points around the circumference at the end of the cylindrical part as shown in FIG. 7. The single measurements (43) are used to calculate the average cylindrical spray dryer outlet temperature.

In one embodiment of the invention the drying gas loop was heated up and the dosage of monomer solution is started up. From this time the spray dryer outlet temperature is controlled to at least 115° C., preferably of at least 117° C. more preferably of 118° C. by adjusting the gas inlet temperature via the heat exchanger (20). The gas inlet temperature is at least 169° C., preferably at least 173° C., more preferably at least 176° C. most preferably 179° C.

In one preferred embodiment a monomer separator unit (38) is used for recycling of the monomers from the condenser column (12) into the monomer feed (35). This monomer separator unit is for example especially a combination of micro-, ultra-, nanofiltration and osmose membrane units, to separate the monomer from water and polymer particles. Suitable membrane separator systems are described, for example, in the monograph "Membranen: Grundlagen, Verfahren und Industrielle Anwendungen", K. Ohlrogge and K. Ebert, Wiley-VCH, 2012 (ISBN: 978-3-527-66033-9).

The product accumulated in the internal fluidized bed (27). Conditioned internal fluidized bed gas is fed to the internal fluidized bed (27) via line (25). In one embodiment of the invention the gas preferably having a temperature of 105° C., more preferably of 106° C. The relative humidity of the internal fluidized bed gas is preferably controlled by the temperature in the condensor column (12) and using the Mollier diagram.

The spray dryer offgas is filtered in a dust separation unit (9) and sent to a condenser column (12) for quenching/cooling. After dust separation (9) a recuperation heat exchanger system for preheating the gas after the condenser column (12) can be used. The dust separation unit (9) may be heat-traced on a temperature of preferably from 80 to 180° C., more preferably from 90 to 150° C., most preferably from 100 to 140° C.

Example for the dust separation unit are baghouse filter, membranes, cyclones, dust compactors and for examples described, for example, in the monographs "Staubabscheiden", F. Löffler, Georg Thieme Verlag, Stuttgart, 1988 (ISBN 978-3137122012) and "Staubabscheidung mit Schlauchfiltern und Taschenfiltern", F. Löffler, H. Dietrich and W. Flatt, Vieweg, Braunschweig, 1991 (ISBN 978-3540670629).

Most preferable are cyclones, for example, cyclones/centrifugal separators of the types ZSA/ZSB/ZSC from LTG Aktiengesellschaft and cyclone separators from Ventilatorenfabrik Oelde GmbH, Camfil Farr International and MikroPul GmbH.

Excess water is pumped out of the condenser column (12) by controlling the (constant) filling level in the condenser column (12). The water in the condenser column (12) is pumped counter-current to the gas via quench nozzles (11) and cooled by a heat exchanger (13) so that the temperature in the condenser column (12) is preferably from 40 to 71° C., more preferably from 46 to 69° C., most preferably from 49 to 65° C. and more even preferably from 51 to 60° C. The water in the condenser column (12) is set to an alkaline pH by dosing a neutralizing agent to wash out vapors of monomer a). Aqueous solution from the condenser column (12) can be sent back for preparation of the monomer solution.

The condenser column offgas may be split to the gas drying unit (37) and the conditioned internal fluidized bed gas (27).

The principle of a gas drying unit is described in the monograph "Leitfaden für Lüftungs- und Kli-maanlagen—Grundlagen der Thermodynamik Komponenten einer Vollklimaanlage Normen und Vorschriften", L. Keller, Oldenbourg Industrieverlag, 2009 (ISBN 978-3835631656). As gas drying unit can be used, for example, an air gas cooling system in combination with a gas mist eliminators or droplet separator (demister), for examples, droplet vane type separator for horizontal flow (e.g. type DH 5000 from Munters AB, Sweden) or vertical flow (e.g. type DV 270 from Munters AB, Sweden). Vane type demisters remove liquid droplets from continuous gas flows by inertial impaction. As the gas carrying entrained liquid droplets moves through the sinusoidal path of a vane, the higher density liquid droplets cannot follow and as a result, at every turn of the vane blades, these liquid droplets impinge on the vane surface. Most of the droplets adhere to the vane wall. When a droplet impinges on the vane blade at the same location, coalescence occurs. The coalesced droplets then drain down due to gravity.

As air gas cooling system, any gas/gas or gas/liquid heat exchanger can be used. Preferred are sealed plate heat exchangers.

The water, which is condensed in the gas drying unit (37) can be partially used as wash water for the condenser column (12) or disposed.

The gas temperatures are controlled via heat exchangers (20) and (22). The hot drying gas is fed to the cocurrent spray dryer via gas distributor (3). The gas distributor (3) consists preferably of a set of plates providing a pressure drop of preferably 1 to 100 mbar, more preferably 2 to 30 mbar, most preferably 4 to 20 mbar, depending on the drying gas amount. Turbulences and/or a centrifugal velocity can also be introduced into the drying gas if desired by using gas nozzles or baffle plates.

Conditioned internal fluidized bed gas is fed to the internal fluidized bed (27) via line (25). The steam content of the fluidized bed gas can be controlled by the temperature in the condenser column (12). The product holdup in the internal fluidized bed (27) can be controlled via rotational speed of the rotary valve (28).

The amount of gas in the internal fluidized bed (27) is selected so that the particles move free and turbulent in the internal fluidized bed (27). The product height in the internal fluidized bed (27) is with gas preferably at least 10%, more preferably at least 20%, more preferably at least 30%, even more preferably at least 40% higher than without gas.

The product is discharged from the internal fluidized bed (27) via rotary valve (28). The product holdup in the internal fluidized bed (27) can be controlled via rotational speed of the rotary valve (28). The sieve (29) is used for sieving off overs/lumps.

The monomer solution is preferably prepared by mixing first monomer a) with a neutralization agent and secondly with crosslinker b). The temperature during neutralization is controlled to preferably from 5 to 60° C., more preferably from 8 to 40° C., most preferably from 10 to 30° C., by using a heat exchanger and pumping in a loop. A filter unit is preferably used in the loop after the pump. The initiators are metered into the monomer solution upstream of the dropletizer by means of static mixers (31) and (32) via lines (33) and (34) as shown in FIG. 6. Preferably a peroxide solution having a temperature of preferably from 5 to 60° C., more preferably from 10 to 50° C., most preferably from 15 to 40° C., is added via line (33) and preferably an azo initiator solution having a temperature of preferably from 2 to 30° C., more preferably from 3 to 15° C., most preferably from 4 to 8° C., is added via line (34). Each initiator is preferably pumped in a loop and dosed via control valves to each dropletizer unit. A second filter unit is preferably used after the static mixer (32). The mean residence time of the monomer solution admixed with the full initiator package in the piping before dropletization is preferably less than 60 s, more preferably less than 30 s, most preferably less than 10 s.

For dosing the monomer solution into the top of the spray dryer preferably three dropletizer units are used as shown in FIG. 4 of WO 2016/134905 A1. However, any number of dropletizers can be used that is required to optimize the throughput of the process and the quality of the product. Hence, in the present invention at least one dropletizer is employed, and as many dropletizers as geometrically allowed may be used.

A dropletizer unit consists of an outer pipe (47) having an opening for the dropletizer cassette (49) as shown in FIG. 7 of WO2016/134905A1. The dropletizer cassette (49) is connected with an inner pipe (48). The inner pipe (48) having a PTFE block (50) at the end as sealing can be pushed in and out of the outer pipe (51) during operation of the process for maintenance purposes.

The temperature of the dropletizer cassette (57) is controlled to preferably 5 to 80° C., more preferably 10 to 70° C., most preferably 30 to 60° C., by water in flow channels (55) as shown in FIG. 8 of WO2016/134905A1.

The dropletizer cassette has preferably from 10 to 2000 bores, more preferably from 50 to 1500 bores, most preferably from 100 to 1000 bores. The diameter of the bores size area is 1900 to 22300µ², more preferably from 7800 to 20100 µm², most preferably from 11300 to 17700 µm². The bores can be of circular, rectangular, triangular or any other shape. Circular bores are preferred with a bore size from 50 to 170 µm, more preferably from 100 to 160 µm, most preferably from 120 to 150 µm. The ratio of bore length to bore diameter is preferably from 0.5 to 10, more preferably from 0.8 to 5, most preferably from 1 to 3. The droplet plate (53) can have a greater thickness than the bore length when using an inlet bore channel. The droplet plate (53) is preferably long and narrow as disclosed in WO 2008/086976 A1. Multiple rows of bores per droplet plate can be used, preferably from 1 to 20 rows, more preferably from 2 to 5 rows.

The dropletizer cassette (57) consists of a flow channel (56) having essential no stagnant volume for homogeneous distribution of the premixed monomer and initiator solutions and two droplet plates (53). The droplet plates (53) have an angled configuration with an angle of preferably from 1 to 90°, more preferably from 3 to 45°, most preferably from 5 to 20°. Each droplet plate (53) is preferably made of a heat and/or chemically resistant material, such as stainless steel, polyether ether ketone, polycarbonate, polyarylsulfone, such as polysulfone, or polyphenylsulfone, or fluorous polymers, such as perfluoroalkoxyethylene, polytetrafluoroethylene, polyvinylidenfluorid, ethylene-chlorotrifluoroethylene copolymers, ethylene-tetrafluoroethylene copolymers and fluorinated polyethylene. Coated droplet plates as disclosed in WO 2007/031441 A1 can also be used. The choice of material for the droplet plate is not limited except that droplet formation must work and it is preferable to use materials which do not catalyze the start of polymerization on its surface.

Figure 5:
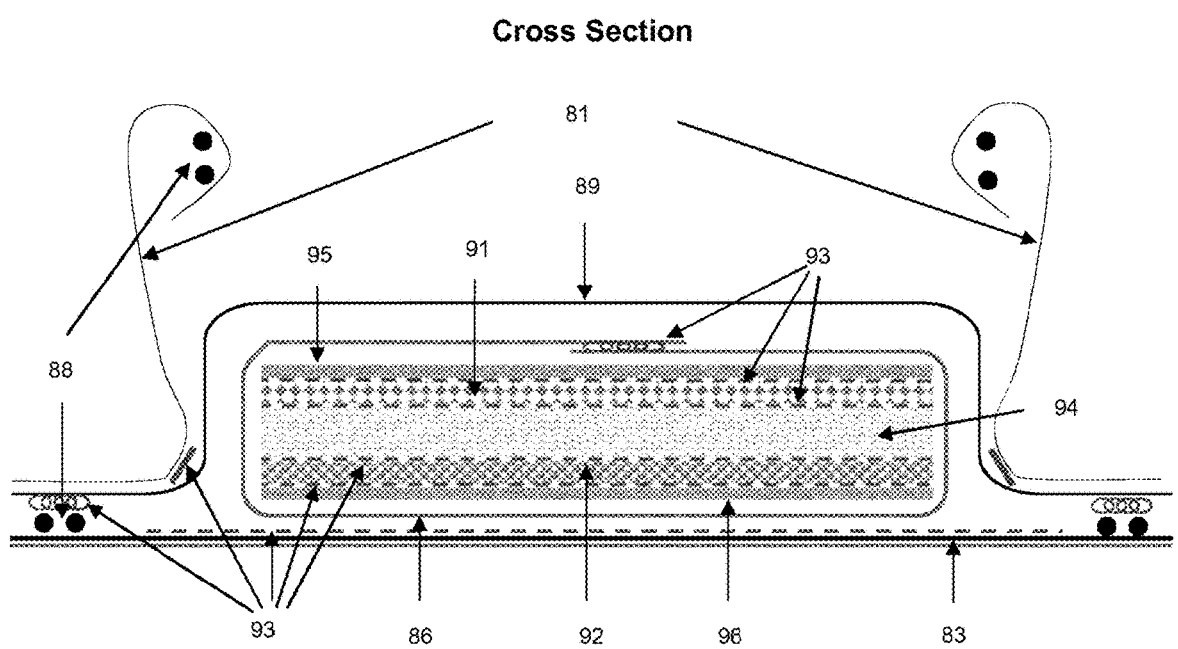
FIG. 5 illustrates a schematic view of a fluid absorbent article.

The arrangement of dropletizer cassettes is preferably rotationally symmetric or evenly distributed in the spray dryer (for example see FIGS. 4 to 5 of WO 2016/134905 A1).

In a preferred embodiment the angle configuration of the droplet plate (53) is in the middle lower then outside, for example: 4a=3°, 4b=5° and 4c=8° (FIG. 6 of WO 2016/134905 A1).

The throughput of monomer including initiator solutions per dropletizer unit is preferably from 10 to 4000 kg/h, more preferably from 100 to 1000 kg/h, most preferably from 200 to 600 kg/h. The throughput per bore is preferably from 0.1 to 10 kg/h, more preferably from 0.5 to 5 kg/h, most preferably from 0.7 to 2 kg/h.

The present invention provides water-absorbent polymer particles H.

In one embodiment the water-absorbent polymer particles H having a CRC of 38 g/g to 85 g/g, preferably of 40 g/g to 80 g/g, more preferably of 42 g/g to 75 g/g.

In one embodiment of the invention the water-absorbent polymer particles H having a vortex of 40 s or less, preferably of 35 s or less, more preferably of 30 s or less.

According to the invention the water-absorbent polymer particles H having a vortex of 5 to 40 s, preferably of 8 to 35 s.

According to the invention the water-absorbent polymer particles H having an AUL (21 g cm$^{-2}$) of 22 g/g to 60 g/g, preferably of 25 g/g to 60 g/g, more preferably of 27 g/g to 58 g/g, most preferably of at least 28 g/g to 55 g/g According to the invention the water-absorbent polymer particles H within the absorbent core (80) having a VAUL (i=21 g cm$^{-2}$) of 1000 s or less, preferable of 700 s or less, more preferable of 500 s or less.

In one embodiment of the invention the fluid absorbent core (80) comprising water-absorbent polymer particles H having a $T_{20}$ of 1000 s or less, preferably of 900 s or less, more preferable of 800 s or less, most preferable of 700 s or less.

The inventive fluid absorbent core (80) comprising water-absorbent polymer particles H having a FSC (1 min) of at least 25 g/g/s, preferably at least 27 g/g/s, more preferably at least 28 g/g/s, most preferably at least 30 g/g/s.

The water-absorbent polymer particles H within the inventive fluid absorbent core (80) having a SAP-Rewet (3 min) of 1.5 g or less, preferably of 1.3 g or less, more preferably of 1.1 g or less, most preferably of 1.0 g or less.

The water-absorbent polymer particles H having a roundness from 0.79 to 0.85, preferably from 0.80 to 0.85, more preferably from 0.80 to 0.84 most preferably from 0.80 to 0.83. The roundness is the volume-average roundness.

The water-absorbent polymer particles H within the inventive fluid absorbent core (80) having an extractables content (16h) of 10 wt % or less, preferably 8.5 wt/% or less, more preferably 7 wt % or less, most preferably 6 wt % or less.

According to the invention the water-absorbent polymer particles H are surface-crosslinked.

The water-absorbent polymer particles H particularly suitable for a fluid absorbent core (80) according to any of claims 1 to 12.

Fluid-Absorbent Core (80)—Absorbent Paper

An absorbent core (80) according to the invention comprises at least one preferably at least two layers of water-absorbent polymer particles. One of the at least two layers of water-absorbent polymer particles laid on top side (91) and another laid on the bottom (92).

A first water-absorbent polymer or a blend of water absorbent polymers (91) is dropped onto one side of a nonwoven material (94). An adhesive (93) is applied to the upper layer (top tissue layer) (95). The tissue layer (95) is laminated with the side of the nonwoven (94) carrying the water-absorbent polymer (91). A second water-absorbent polymer (92) is dropped onto the other side of the nonwoven (94). An adhesive (93) is applied to the bottom layer (lower tissue layer) (96). The tissue layer (96) is laminated with the side of the nonwoven (94) carrying the water-absorbent polymer (92).

FIG. 4 illustrates an absorbent core according to the invention.

In order to increase the integrity of the fluid-absorbent core (80), the core may optionally provided with a cover

(86) (e.g. tissue wrap). This cover (86) may be at the top and/or at the bottom of the fluid-absorbent core (80) with bonding at lateral juncture and/or bonding at the distal juncture by hot-melt, ultrasonic bonding, thermal bonding or combination of bonding techniques know to persons skilled in the art. Further, this cover (86) may include the whole fluid-absorbent core with a unitary sheet of material and thus function as a wrap. Wrapping is possible as a full wrap, a partial wrap or as a C-Wrap.

A schematic view of one embodiment of the inventive absorbent core (80) is shown in FIG. 4.

The material of the core cover (86) may comprise any known type of substrate, including nonwovens, webs, garments, textiles, films, tissues and laminates of two or more substrates or webs. The core cover material may comprise natural fibers, such as cellulose, cotton, flax, linen, hemp, wool, silk, fur, hair and naturally occurring mineral fibers. The core cover material may also comprise synthetic fibers such as rayon and lyocell (derived from cellulose), polysaccharides (starch), polyolefin fibers (polypropylene, polyethylene), polyamides, polyester, butadienestyrene block copolymers, polyurethane and combinations there-of. Preferably, the core cover (86) comprises synthetic fibers or tissue.

The fibers may be mono- or multicomponent. Multicomponent fibers may comprise a homo-polymer, a copolymer or blends thereof.

According to the invention the absorbent core (80) comprises at least two thin and flexible single layers (91, 92) of suitable absorbent material. Each of these layers is macroscopically two-dimensional and planar and of very low thickness compared to the other dimensions. Said layer may incorporate superabsorbent material throughout the layer.

The layers may have different concentrations and different water-absorbent polymer material showing concentrations in the range from about 90 to 100% by weight, preferably 95 to 100% by weight, more preferably 98 to 100% by weight.

The layers (91, 92) are preferably joined to the upper and/or bottom layer (95, 96) respectively e.g. by addition of adhesives (93) or by mechanical, thermal or ultrasonic bonding or combinations thereof, whereas adhesives are preferred.

According to another embodiment of the invention at least one of the layers (91) and/or (92) containing a blend of at least two kinds of water-absorbent polymer particles.

Furthermore, it is preferred that the water-absorbent polymer particles are placed within the core (80), especially within each layer (91, 92) in discrete regions, chambers or pockets, e.g. supported by at least an adhesive. Techniques of application of the water-absorbent polymer materials into the absorbent core especially in the respective layers (91, 92) are known to persons skilled in the art and may be volumetric, loss-in-weight or gravimetric. Known techniques include the application by vibrating systems, single and multiple auger systems, dosing roll, weigh belt, fluid bed volumetric systems and gravitational sprinkle and/or spray systems. Further techniques of insertion are falling dosage systems consensus and contradictory pneumatic application or vacuum printing method of applying the fluid absorbent polymer materials.

The quantity of water-absorbent polymer particles within the fluid-absorbent core (80) is from 100 to 500 gsm, preferably 200 to 400 gsm, more preferably 250 to 300 gsm in case of maxi diapers (size L), wherein each layer contains at least 50 gsm water absorbent polymer particles preferably at least 100 gsm water absorbent polymer particles The absorbent core (80) may comprise also at least one layer of other material such as short-fiber air-laid nonwoven materials (94); nonwoven materials such as polyethylene, polypropylene, nylon, polyester, and the like; cellulosic fibrous materials such as paper tissue or towels known in the art, wax-coated papers, corrugated paper materials, and the like; or fluff pulp. Said layer may further incorporate bi-component binding fibers.

The nonwoven (94) within in the absorbent core (80) is typically a single layer, e.g. made by air-thru bonded process. Its total basis weight is around 10 to 100 gsm, preferably 40 to 60.

The absorbent core (80) additionally may comprise at least two tissue layers (95, 96). The tissue layers are not restricted to tissue material such as paper it also refers to nonwovens.

The material of the layers (95, 96) may comprise any known type of substrate, including webs, garments, textiles and films. The tissue layers (95, 96) may comprise natural fibers, such as cellulose, cotton, flax, linen, hemp, wool, silk, fur, hair and naturally occurring mineral fibers. The tissue layer (95, 96) may also comprise synthetic fibers such as rayon and lyocell (de-rived from cellulose), polysaccharides (starch), polyolefin fibers (polypropylene, polyethylene), polyamides, polyester, butadiene-styrene block copolymers, polyurethane and combinations thereof. Preferably, the tissue layer comprises cellulose fibers. It is preferred that the tissue layer is made from ca. 50% wood pulp and 50% chemical viscose fibers at >45 gsm to provide tensile strength and integrity.

According to the invention the upper and lower tissue layers (95, 96) each total basis weight is from 10 to 100 gsm, preferably 30 to 80 gsm.

According to the invention it is preferred that the fluid-absorbent core (80) comprises not more than 20% by weight of an adhesive, preferably not more than 10% by weight of an adhesive, more preferably not more than 5% by weight. Preferably the adhesive is a hotmelt adhesive.

The absorbent core (80) respectively has a total basis weight ranging from about 150 gsm to about 2000 gsm, preferably from about 300 gsm to about 750 gsm, and more preferably from about 500 gsm to about 650 gsm.

According to the present invention the fluid absorbent core (80) comprising at least one absorption layer, the layer comprising at least 80% by weight of water-absorbent polymer particles, preferably at least 90% by weight, more preferably at least 95% by weight, most preferably at least 98% by weight of water-absorbent polymer particles; 0 to 10% by weight of an adhesive, preferably 0 to 5% by weight of an adhesive and from 0 to 10% by weight, preferably 0 to 5% by weight, more preferably 0 to 2% by weight of fibrous material, wherein the water-absorbent polymer particles within the absorption layer are water-absorbent polymer particles H having a vortex of 40 s or less and having a roundness of 0.79 to 0.85 and/or a CRC of 38 g/g to 85 g/g.

According to the invention it is preferred that the fluid-absorbent core (80) comprises at least two absorption layers, an upper layer (91) and a bottom layer (92), wherein at least the bottom layer (92) comprises water-absorbent polymer particles H having a vortex of 40 s or less and having a roundness of 0.79 to 0.85 and/or a CRC of 38 g/g to 85 g/g. Each of the layers upper layer (91) and bottom (lower) layer (92) comprising at least 80% by weight of water-absorbent polymer particles, preferably at least 90% by weight, more preferably at least 95% by weight, most preferably at least 98% by weight of water-absorbent polymer particles; 0 to 10% by weight of an adhesive, preferably 0 to 5% by weight of an adhesive and from 0 to 10% by weight, preferably 0 to 5% by weight, more preferably 0 to 2% by weight of fibrous material.

In one preferred embodiment of the invention the water-absorbent polymer particles H having a CRC of 38 g/g to 85 g/g, preferably of 40 g/g to 80 g/g, more preferably of 42 g/g to 75 g/g.

In one embodiment of the invention the water-absorbent polymer particles H having a vortex of 40 s or less, preferably of 35 s or less, more preferably of 30 s or less.

In another preferred embodiment of the invention the water-absorbent polymer particles H having a vortex of 5 to 40 s, preferably of 8 to 35 s.

According to the invention the water-absorbent polymer particles H having an AUL (21 g cm$^{-2}$) of 22 g/g to 60 g/g, preferably of at least 25 g/g to 60 g/g, more preferably of 27 g/g to 58 g/g, most preferably of at least 28 g/g to 55 g/g.

According to the invention the water-absorbent polymer particles H within the absorbent core (80) having a VAUL (i=21 g cm$^{-2}$) of 1000 s or less, preferable of 700 s or less, more preferable of 500 s or less.

In one embodiment of the invention the fluid absorbent core (80) comprising water-absorbent polymer particles H having a $T_{20}$ of 1000 s or less, preferably of 900 s or less, more preferable of 800 s or less, most preferable of 700 s or less.

The inventive fluid absorbent core (80) comprising water-absorbent polymer particles H having a FSC (1 min) of at least 25 g/g/s, preferable at least 27 g/g/s, more preferable at least 28 g/g/s, most preferably at least 30 g/g/s.

The water-absorbent polymer particles H within the inventive fluid absorbent core (80) having a SAP-Rewet (3 min) of 1.5 g or less, preferably of 1.3 g or less, more preferably of 1.1 g or less, most preferably of 1.0 g or less.

The inventive fluid absorbent core (80) comprising water-absorbent polymer particles H having a roundness from 0.79 to 0.85, preferably from 0.80 to 0.85, more preferably from 0.80 to 0.84 most preferably from 0.80 to 0.83. The roundness is the volume-average roundness.

The water-absorbent polymer particles H within the inventive fluid absorbent core (80) having an extractables content (16$h$) of of 10 wt % or less, preferably 8.5 wt/% or less, more preferably 7 wt % or less, most preferably 6 wt % or less According to the invention the water-absorbent polymer particles H are surface-crosslinked.

One preferred fluid-absorbent core (80) according to the invention comprises within the lower layer (92) water-absorbent polymer particles H with a CRC of 38 g/g to 85 g/g and a vortex of 40 s or less, preferably with a CRC of 40 g/g to 80 g/g and a vortex of 35 s or less, more preferably with a CRC of 42 g/g to 75 g/g and a vortex of 35 s or less.

Also preferred are a fluid-absorbent core (80) according to the invention comprising within the lower layer (92) water-absorbent polymer particles H with a vortex of 40 s or less and a roundness from 0.79 to 0.85, preferably with a vortex of 35 s or less and a roundness from 0.80 to 0.85, more preferably with a vortex of 35 s or less and a roundness from 0.80 to 0.84.

Another preferred fluid-absorbent core (80) according to the invention comprises within the lower layer (92) water-absorbent polymer particles H with a CRC of 38 g/g to 85 g/g and a vortex of 40 s or less and a roundness from 0.79 to 0.85, preferably with a CRC of 40 g/g to 80 g/g and a vortex of 35 s or less and a roundness from 0.80 to 0.85, more preferably with a CRC of 42 g/g to 75 g/g and a vortex of 35 s or less and a roundness from 0.80 to 0.84.

Vortex and CRC could be e.g. adapted by modifying crosslink density or particle size distribution of the water-absorbent polymer particles.

According to one embodiment of the invention the Water Pouring Time of the inventive the flu-id absorbent core (80) is 28 s or less, preferably 26 s, more preferably 25 s or less and the Water Pouring Rewet the fluid absorbent core (80) is 3.5 g or less, preferably 3.3 or less, measured according to the method "Water pouring test" disclosed herein.

The inventive absorbent core absorbs a fluid very fast (Water Pouring Time) coupled with a low rewet. This means the absorbed fluid is quickly absorbed and hold within the core even under pressure.

According to the invention the fluid absorbent core (80) having a Liquid Diffusion Length of at least 245 mm, preferably at least 250 mm, more preferably above 260 mm, most preferably above 270 mm, a total strike-thru time of 50 s or less, preferably of 48 s or less, more preferably of 45 s or less and a Total Rewet of 40 g or less, preferably of 35 g or less, more preferably of 30 g or less measured according to the method "Strike-thru/Rewet" disclosed in the description.

Especially the Liquid Diffusion Length of at least 245 mm shows that the fluid within the inventive absorbent core is distributed throughout the core. The fluid does not stick in only a small part of the core. So the whole core area is used and gel blocking is prevented.

The fluid-absorbent core (80) typically has a uniform size or profile. Suitable fluid-absorbent cores can also have profiled structures, concerning the shape of the core and/or the content of water-absorbent polymer particles and/or the distribution of the water-absorbent polymer particles and/or the dimensions of the different layers if a layered fluid-absorbent core is present.

The shape of the core in view from above (x-y dimension) can be rectangular, anatomical shaped with a narrower crotch area or any other shapes.

The top view area of the fluid-absorbent core (80) is preferably at least 200 cm$^2$, more preferably at least 250 cm$^2$, most preferably at least 300 cm$^2$. The top view area is the part of the core that is face-to-face to the upper liquid-pervious layer.

The fluid-absorbent core may comprise additional additives typically present in fluid absorbent articles known in the art. Exemplary additives are fibers for reinforcing and stabilizing the fluid-absorbent core. Preferably polyethylene is used for reinforcing the fluid-absorbent core.

Further suitable stabilizer for reinforcing the fluid-absorbent core are materials acting as binder.

In varying the kind of binder material or the amount of binder used in different regions of the flu-id-absorbent core it is possible to get a profiled stabilization. For example, different binder materials exhibiting different melting temperatures may be used in regions of the fluid-absorbent core, e.g. the lower melting one in the central region of the core, and the higher melting in the distal regions.

Suitable binder materials may be adhesive or non-adhesive fibers, continuously or discontinuously extruded fibers, bi-component staple fibers, non-elastomeric fibers and sprayed liquid binder or any combination of these binder materials.

Further, thermoplastic compositions usually are added to increase the integrity of the core layer. Thermoplastic compositions may comprise a single type of thermoplastic polymers or a blend of thermoplastic polymers. Alternatively, the thermoplastic composition may comprise hot melt adhesives comprising at least one thermoplastic polymer together with thermoplastic diluents such as tackifiers, plasticizers or other additives, e.g. antioxidants. The thermoplastic composition may further comprise pressure sensitive hot melt adhesives comprising e.g. crystalline polypropylene and an amorphous polyalphaolefin or styrene block copolymer and mixture of waxes.

Concerning odor control, perfumes and/or odor control additives are optionally added. Suitable odor control additives are all substances of reducing odor developed in carrying fluid-absorbent articles over time known in the art. Thus, suitable odor control additives are inorganic materials, such as zeolites, activated carbon, bentonite, silica, aerosile, kieselguhr, clay; chelants such as ethylenediamine tetraacetic acid (EDTA), cyclodextrins, aminopolycarbonic acids, ethylenediamine tetramethylene phosphonic acid, aminophosphate, polyfunctional aromates, N,N-disuccinic acid. Suitable odor control additives are further antimicrobial agents.

Suitable odor control additives are further compounds with anhydride groups such as maleic-, itaconic-, polymaleic- or polyitaconic anhydride, copolymers of maleic acid with C2-C8 olefins or styrene, polymaleic anhydride or copolymers of maleic anhydride with isobutene, di-isobutene or styrene, compounds with acid groups such as ascorbic, benzoic, citric, salicylic or sorbic acid and fluid-soluble polymers of monomers with acid groups, homo- or co-polymers of C3-C5 mono-unsaturated carboxylic acids.

Newest developments propose the addition of wetness indication additives.

Suitable wetness indication additives comprising a mixture of sorbitan monooleate and polyethoxylated hydrogenated castor oil. Preferably, the amount of the wetness indication additive is in the range of about 0.0001 to 2% by weight related to the weight of the fluid-absorbent core.

According to the invention an absorbent core (80) comprises top (91) and bottom (92) layers of water-absorbing polymer particles containing each 100 to 200 per square meter (g/m² or gsm), preferably 120 to 160 gsm, most preferably 130 to 150 gsm Both layers are glued (93) with 1 to 0.2 gsm, preferably 0.7 to 0.3 gsm, more preferably 0.6 to 0.4 gsm hot melt adhesive on 100 to 30 gsm, preferably 80 to 40 gsm, more preferably 45 to 60 gsm air-thru-bond nonwoven material (94) and are then sandwiched with two layers of 70 to 20 gsm, preferably 60 to 30 gsm, more preferably 40 to 50 gsm condensed tissue layers on the top (95) and bottom (96) using hot-melt glue applied to the surface at 2.4 to 1.0 gsm, preferably 2.3 to 1.5 gsm, more preferably 2.2 to 1.8 gsm. Total hot-melt glue used is 2.5 g/m² each for both top and bottom layers. Numbers refer to FIG. 4

A standard process to manufacture Absorbent Paper laminate cores is described in the following: Adhesive (2) (preferably hot melt adhesive) is sprayed on to tissue (1) (e.g. condensed tissue). Superabsorbent SAP (3) or (4) or both is applied on to high loft nonwoven material ATB (7) (e. g. air-through bond nonwoven of polyester) using roller feeder (commercially available SAP feeder roller type). The nonwoven containing SAP is then laminated with the tissue layer (1) on which the adhesive was applied, at position (10).

Adhesive (8) (preferably hot melt adhesive) is sprayed on to tissue (9). Superabsorbent SAP (5) or (6) or both is applied on to the other side of the high loft nonwoven material ATB (7). The nonwoven containing SAP is then laminated with the tissue layer (9) on which the adhesive was applied, at position (15).

Figure 2:
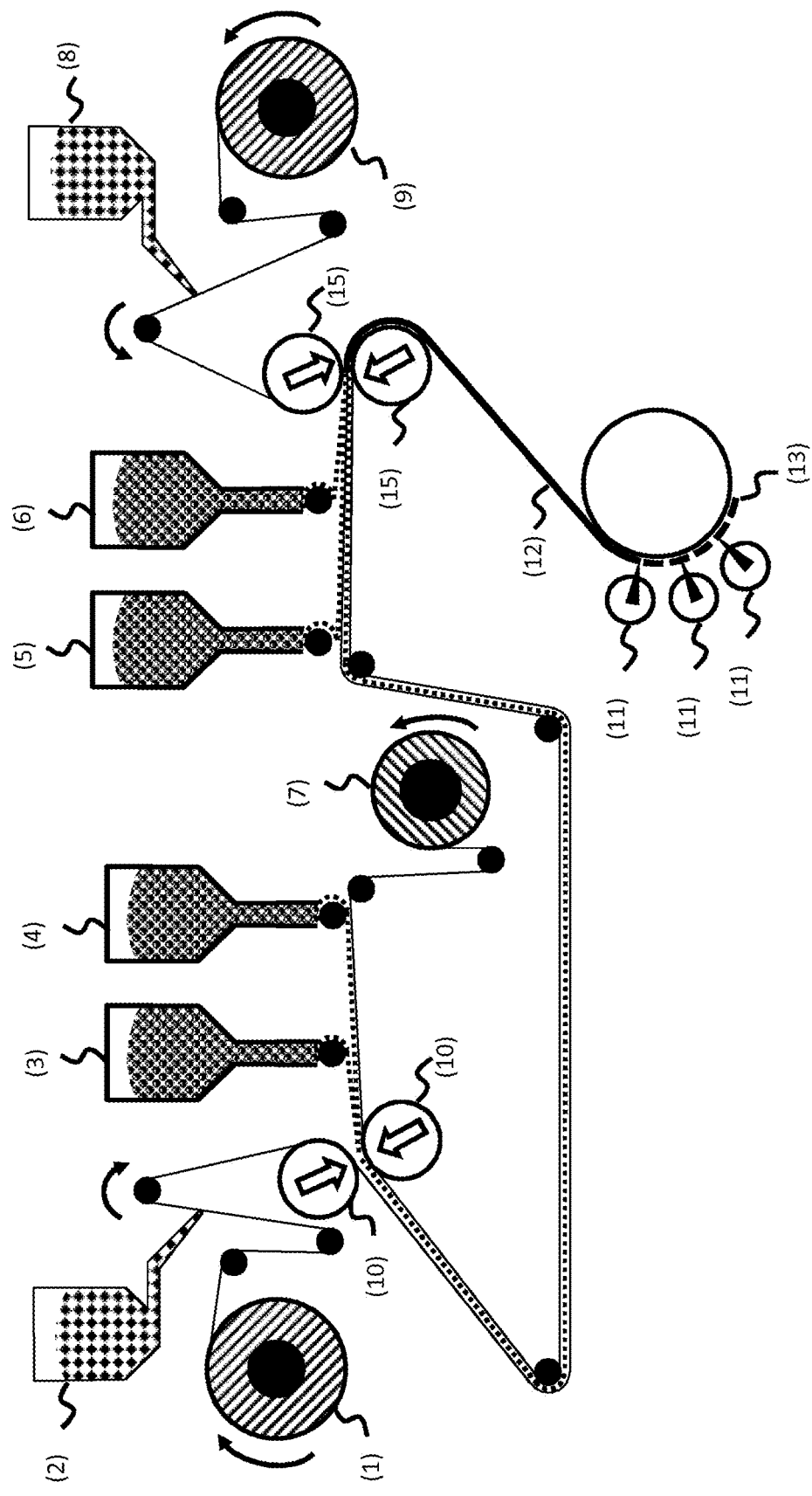
FIG. 2 illustrates a standard process to manufacture absorbent paper laminate cores.

This gives a 5-layer absorbent paper structure; the laminate finally is cut into desired width by slitter (11). The numbers refer to FIG. 2:

According to the invention a preferred absorbent core (80) comprises top (91) and bottom (92) layers of water-absorbing polymer particles containing each 130 grams per square meter (g/m² or gsm) with a 50 g/m² air-thru-bond nonwoven material (94) in between the two layers (91) and (92). Both layers are then sandwiched with two layers of 45 g/m² condensed tissue layers on the top (95) and bottom (96) using hot-melt glue (93) applied to the surface at 2.5 g/m². Total hot-melt glue used is 2.5 g/m² each for both top and bottom layers. The numbers refer to FIG. 4.

The density of the fluid-absorbent core is in the range of 0.1 to 0.25 g/cm³, preferably 0.1 to 0.28 g/cm³. The thickness of the fluid-absorbent core is in the case of diapers in the range of 1 to 8 mm, preferably 1 to 5 mm, more preferably 1.5 to 3 mm, in the case of adult-incontinence products in the range of 3 to 15 mm.

Fluid-Absorbent Article

According to the invention the inventive fluid-absorbent core is part of a fluid-absorbent article.

According to the invention a fluid-absorbent article comprises
(A) an upper liquid-pervious layer (89)
(B) a lower liquid-impervious layer (83)
(C) a fluid-absorbent core (80) according to the invention between (89) and (83) comprising at least one layer, wherein the layer comprising from 0 to 10% by weight a fibrous material and from 90 to 100% by weight water-absorbent polymer particles;
preferably from 0 to 5% by weight a fibrous material and from 95 to 100% by weight water-absorbent polymer particles;
more preferably from 0 to 5% by weight a fibrous material and from 95 to 100% by weight water-absorbent polymer particles; most preferably 0% by weight a fibrous material and 100 by weight water absorbent polymer particles;
based on the sum of water-absorbent polymer material and fibrous material,
(D) an optional acquisition-distribution layer (70) between (A) and (C) and
(F) other optional components.

According to another embodiment of the invention a fluid-absorbent article comprises
(A) an upper liquid-pervious layer (89)
(B) a lower liquid-impervious layer (83)
(C) a fluid-absorbent core (80) according to the invention between (89) and (83) comprising at least two layers, wherein each layer comprising from 0 to 10% by weight a fibrous material and from 90 to 100% by weight water-absorbent polymer particles;
preferably from 0 to 5% by weight a fibrous material and from 95 to 100% by weight water-absorbent polymer particles;
more preferably from 0 to 5% by weight a fibrous material and from 95 to 100% by weight water-absorbent polymer particles; most preferably 0% by weight a fibrous material and 100 by weight water absorbent polymer particles;
based on the sum of water-absorbent polymer material and fibrous material,
(D) an optional acquisition-distribution layer (70) between (A) and (C) and
(F) other optional components.

The fluid-absorbent core (80) is disposed between the upper liquid-pervious sheet (89) and the lower liquid-impervious sheet (83).

Fluid-absorbent articles are understood to mean, for example, incontinence pads and incontinence briefs for adults or diapers and training pants for babies. Suitable fluid-absorbent articles including fluid-absorbent compositions comprising fibrous materials and optionally water-absorbent polymer particles to form fibrous webs or matrices for the substrates, layers, sheets and/or the fluid-absorbent core.

Suitable fluid-absorbent articles are composed of several layers whose individual elements must show preferably definite functional parameter such as dryness for the upper liquid-pervious layer (89), vapor permeability without wetting through for the lower liquid-impervious layer (83), a flexible, vapor permeable and thin fluid-absorbent core (80), showing fast absorption rates and being able to retain highest quantities of body fluids, and an optional acquisition-distribution layer (70) between the upper layer (89) and the core (80), acting as transport and distribution layer of the discharged body fluids. These individual elements are combined such that the resultant fluid-absorbent article meets overall criteria such as flexibility, water vapor breath-ability, dryness, wearing comfort and protection on the user facing side, and concerning liquid retention, rewet and prevention of wet through on the garment side. The specific combination of these layers provides a fluid-absorbent article delivering both high protection levels as well as high comfort to the consumer.

Methods to make fluid absorbent articles are for example described in the following publications and literature cited therein and are expressly incorporated into the present invention: EP 2 301 499 A1, EP 2 314 264 A1, EP 2 387 981 A1, EP 2 486 901 A1, EP 2 524 679 A1, EP 2 524 679 A1, EP 2 524 680 A1, EP 2 565 031 A1, U.S. Pat. No. 6,972,011, US 2011/0162989, US2011/0270204, WO 2010/004894 A1, WO 2010/004895 A1, WO 2010/076857 A1, WO2010/082373 A1, WO 2010/118409 A1, WO 2010/133529 A2, WO 2010/143635 A1, WO2011/084981 A1, WO 2011/086841 A1, WO 2011/086842 A1, WO 2011/086843 A1, WO2011/086844 A1, WO 2011/117997 A1, WO 2011/136087 A1, WO 2012/048879 A1, WO2012/052173 A1 and WO 2012/052172 A1.

FIG. 5 is a schematic view of a fluid absorbent article according to the invention: The fluid-absorbent article comprises an absorbent core (80) comprising at least two layers of water-absorbent polymer particles, top (91), bottom (92) optionally sandwiched by at least two tissue layers, top (95) and bottom (96) and at least one nonwoven (94) (e.g. high loft air thru bond nonwoven) sandwiched by the at least two layers of water-absorbent polymer particles (91, 92). The layers optionally be connected to each other (93), e. g. by adhesive, ultrasonic bonding or any other suitable method. The total core structure (80) is optionally sur-rounded/wrapped by a further nonwoven sheet or tissue layer (86), the so called core wrap, also optionally connected by an adhesive to the sandwich structured absorbent core (80).

Furthermore, the absorbent article comprises an acquisition distribution layer (70) on top of the core (80) or core wrap (86) respectively below the upper liquid-pervious sheet (89) (e. g. embossed spunbond nonwoven), and a lower liquid-impervious sheet (83). Leg cuffs (81) and some elastics (88) may be also present.

Liquid-Pervious Sheet or Liquid Pervious Layer (89)

The liquid-pervious sheet (89) is the layer which is in direct contact with the skin. Thus, the liquid-pervious sheet (89) is preferably compliant, soft feeling and non-irritating to the consumer's skin. Generally, the term "liquid-pervious" is understood thus permitting liquids, i.e. body fluids such as urine, menses and/or vaginal fluids to readily penetrate through its thick-ness. The principle function of the liquid-pervious sheet (89) is the acquisition and transport of body fluids from the wearer towards the fluid-absorbent core. Typically, liquid pervious layers (89) are formed from any materials known in the art such as nonwoven material, films or combinations thereof. Suitable liquid-pervious sheets (89) consist of customary synthetic or semisynthetic fibers or bi-component fibers or films of polyester, polyolefins, rayon or natural fibers or any combinations thereof. In the case of nonwoven materials, the fibers should generally be bound by binders such as polyacrylates. Additionally, the liquid-pervious sheet may contain elastic compositions thus showing elastic characteristics allowing to be stretched in one or two directions.

Suitable synthetic fibers are made from polyvinyl chloride, polyvinyl fluoride, polytetrafluorethylene, polyvinylidene chloride, polyacrylics, polyvinyl acetate, polyethylvinyl acetate, non-soluble or soluble polyvinyl alcohol, polyolefins such as polyethylene, polypropylene, polyamides, poly-esters, polyurethanes, polystyrenes and the like Examples for films are apertured formed thermoplastic films, apertured plastic films, hydro-formed thermoplastic films, reticulated thermoplastic films, porous foams, reticulated foams, and thermoplastic scrims.

Examples of suitable modified or unmodified natural fibers include cotton, bagasse, kemp, flax, silk, wool, wood pulp, chemically modified wood pulp, jute, rayon, ethyl cellulose, and cellulose acetate.

The fibrous material may comprise only natural fibers or synthetic fibers or any combination thereof. Preferred materials are polyester, rayon and blends thereof, polyethylene, and polypropylene. The fibrous material as a component of the fluid-absorbent compositions may be hydrophilic, hydrophobic or can be a combination of both hydrophilic and hydrophobic fibers.

The selection of the ratio hydrophilic/hydrophobic and accordingly the amount of hydrophilic and hydrophobic fibers within fluid-absorbent composition will depend upon fluid handling properties and the amount of water-absorbent polymer particles of the resulting fluid-absorbent composition.

Examples for hydrophilic fibers are cellulosic fibers, modified cellulosic fibers, rayon, polyester fibers such as polyethylen terephthalate, hydrophilic nylon and the like. Hydrophilic fibers can also be obtained from hydrophobic fibers which are hydrophilized by e. g. surfactant-treating or silica-treating. Thus, hydrophilic thermoplastic fibers derived from polyolefins such as polypropylene, polyamides, polystyrenes or the like by surfactant-treating or silica-treating.

To increase the strength and the integrity of the upper-layer, the fibers should generally show bonding sites, which act as crosslinks between the fibers within the layer.

Technologies for consolidating fibers in a web are mechanical bonding, thermal bonding and chemical bonding. In the process of mechanical bonding the fibers are entangled mechanically, e.g., by water jets (spunlace) to give integrity to the web. Thermal bonding is carried out by means of raising the temperature in the presence of low-melting polymers. Examples for thermal bonding processes are spunbonding, through-air bonding and resin bonding.

Preferred means of increasing the integrity are thermal bonding, spunbonding, resin bonding, through-air bonding and/or spunlace.

In the case of thermal bonding, thermoplastic material is added to the fibers. Upon thermal treatment at least a portion of this thermoplastic material is melting and migrates to intersections of the fibers caused by capillary effects. These intersections solidify to bond sites after cooling and increase the integrity of the fibrous matrix. Moreover, in the case of chemically stiffened cellulosic fibers, melting and migration of the thermoplastic material has the effect of increasing the pore size of the resultant fibrous layer while maintaining its density and basis weight. Upon wetting, the structure and integrity of the layer remains stable. In summary, the addition of thermoplastic material leads to improved fluid permeability of discharged body fluids and thus to improved acquisition properties.

Suitable thermoplastic materials including polyolefins such as polyethylene and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the mentioned polymers.

Suitable thermoplastic fibers can be made from a single polymer that is a monocomponent fiber. Alternatively, they can be made from more than one polymer, e.g., bi-component or multi-component fibers. The term "bicomponent fibers" refers to thermoplastic fibers that comprise a core fiber made from a different fiber material than the shell. Typically, both fiber materials have different melting points, wherein generally the sheath melts at lower temperatures. Bi-component fibers can be concentric or eccentric depending whether the sheath has a thickness that is even or uneven through the cross-sectional area of the bi-component fiber. Advantage is given for eccentric bi-component fibers showing a higher compressive strength at lower fiber thickness. Further bi-component fibers can show the feature "uncrimped" (unbent) or "crimped" (bent), further bi-component fibers can demonstrate differing aspects of surface lubricity.

Examples of bi-component fibers include the following polymer combinations: polyethylene/polypropylene, polyethylvinyl acetate/polypropylene, polyethylene/polyester, polypropylene/polyester, copolyester/polyester and the like.

Suitable thermoplastic materials have a melting point of lower temperatures that will damage the fibers of the layer; but not lower than temperatures, where usually the fluid-absorbent articles are stored. Preferably the melting point is between about 75° C. and 175° C. The typical length of thermoplastic fibers is from about 0.4 to 6 cm, preferably from about 0.5 to 1 cm. The diameter of thermoplastic fibers is defined in terms of either denier (grams per 9000 meters) or dtex (grams per 10 000 meters). Typical thermoplastic fibers have a dtex in the range from about 1.2 to 20, preferably from about 1.4 to 10.

A further mean of increasing the integrity of the fluid-absorbent composition is the spunbonding technology. The nature of the production of fibrous layers by means of spunbonding is based on the direct spinning of polymeric granulates into continuous filaments and subsequently manufacturing the fibrous layer.

Spunbond fabrics are produced by depositing extruded, spun fibers onto a moving belt in a uniform random manner followed by thermal bonding the fibers. The fibers are separated during the web laying process by air jets. Fiber bonds are generated by applying heated rolls or hot needles to partially melt the polymer and fuse the fibers together. Since molecular orientation increases the melting point, fibers that are not highly drawn can be used as thermal binding fibers. Polyethylene or random ethylene/propylene copolymers are used as low melting bonding sites.

Besides spunbonding, the technology of resin bonding also belongs to thermal bonding sub-jects. Using this technology to generate bonding sites, specific adhesives, based on e.g. epoxy, polyurethane and acrylic are added to the fibrous material and the resulting matrix is thermically treated. Thus the web is bonded with resin and/or thermal plastic resins dispersed within the fibrous material.

As a further thermal bonding technology through-air bonding involves the application of hot air to the surface of the fibrous fabric. The hot air is circulated just above the fibrous fabric, but does not push through the fibrous fabric. Bonding sites are generated by the addition of binders. Suitable binders used in through-air thermal bonding include crystalline binder fibers, bi-component binder fibers, and powders. When using crystalline binder fibers or powders, the binder melts entirely and forms molten droplets throughout the nonwoven's cross-section. Bonding occurs at these points upon cooling. In the case of sheath/core binder fibers, the sheath is the binder and the core is the carrier fiber. Products manufactured using through-air ovens tend to be bulky, open, soft, strong, extensible, breathable and absorbent. Through-air bonding followed by immediate cold calendering results in a thick-ness between a hot roll calendered product and one that has been though-air bonded without compression. Even after cold calendering, this product is softer, more flexible and more extensible than area-bond hot-calendered material.

Spunlacing ("hydroentanglement") is a further method of increasing the integrity of a web. The formed web of loose fibers (usually air-laid or wet-laid) is first compacted and prewetted to eliminate air pockets. The technology of spunlacing uses multiple rows of fine high-speed jets of water to strike the web on a porous belt or moving perforated or patterned screen so that the fibers knot about one another. The water pressure generally increases from the first to the last injectors. Pressures as high as 150 bar are used to direct the water jets onto the web. This pressure is sufficient for most of the nonwoven fibers, although higher pressures are used in specialized applications.

The spunlace process is a nonwovens manufacturing system that employs jets of water to entangle fibers and thereby provide fabric integrity. Softness, drape, conformability, and relatively high strength are the major characteristics of spunlace nonwoven In newest researches benefits are found in some structural features of the resulting liquid-pervious layers. For example, the thickness of the layer is very important and influences together with its x-y dimension the acquisition-distribution behaviour of the layer. If there is further some profiled structure integrated, the acquisition-distribution behaviour can be directed depending on the three-dimensional structure of the layer. Thus 3D-polyethylene in the function of liquid-pervious layer is preferred. Suitable techniques to create such 3D structures are e.g. embossing, needle-punching, or stitching.

Thus, suitable liquid-pervious sheets (89) are nonwoven layers formed from the fibers above by thermal bonding, spunbonding, resin bonding or through-air bonding. Further suitable liquid-pervious layers are 3D-polyethylene layers and spunlace.

Preferably the 3D-polyethylene layers and spunlace show basis weights from 12 to 22 gsm.

Acquisition-distribution layer is optional. Many Absorbent Paper diapers do not have an ADL, but advanced topsheets (air-thru bond nonwovens with 3D structure; often a combination of 2 topsheets).

Preferred topsheets, which may also substitute an acquisition-distribution layer are air-thru nonwovens with 3D structure.

Most preferred are the use of 2 layers of topsheets. The outer layer having a 3D structure, the inner one without 3D structure. Both sheets are glued together to prevent that the 3D structure of the outer topsheet layer is destroyed by e.g. any stretching steps during the production process of the fluid-absorbent article e.g. a diaper.

Typically, liquid-pervious sheets (89) extend partially or wholly across the fluid-absorbent structure and can extend into and/or form part of all the preferred sideflaps, side wrapping elements, wings and ears.

Liquid-Impervious Sheet or Liquid Impervious Layer (83)

The liquid-impervious sheet (83) prevents the exudates absorbed and retained by the flu-id-absorbent core from wetting articles which are in contact with the fluid-absorbent article, as for example bedsheets, pants, pyjamas and undergarments. The liquid-impervious sheet (83) may thus comprise a woven or a nonwoven material, polymeric films such as thermoplastic film of polyethylene or polypropylene, or composite materials such as film-coated nonwoven material.

Suitable liquid-impervious sheets (83) include nonwoven, plastics and/or laminates of plastic and nonwoven. Both, the plastics and/or laminates of plastic and nonwoven may appropriately be breathable, that is, the liquid-impervious layer (83) can permit vapors to escape from the fluid-absorbent material. Thus the liquid-impervious sheet has to have a definite water vapor transmission rate and at the same time the level of impermeability. To combine these features, suitable liquid-impervious layers including at least two layers, e.g. laminates from fibrous nonwoven having a specified basis weight and pore size, and a continuous three-dimensional film of e.g. polyvinylalcohol as the second layer having a specified thickness and optionally having pore structure. Such laminates acting as a barrier and showing no liquid transport or wet through. Thus, suitable liquid-impervious layers comprising at least a first breathable layer of a porous web which is a fibrous nonwoven, e.g. a composite web of a meltblown nonwoven layer or of a spunbonded nonwoven layer made from synthetic fibers and at least a second layer of a resilient three dimensional web consisting of a liquid-impervious polymeric film, e.g. plastics optionally having pores acting as capillaries, which are preferably not perpendicular to the plane of the film but are disposed at an angle of less than 90° relative to the plane of the film.

Suitable liquid-impervious sheets are permeable for vapor. Preferably the liquid-impervious sheet is constructed from vapor permeable material showing a water vapor transmission rate (WVTR) of at least about 100 gsm per 24 hours, preferably at least about 250 gsm per 24 hours and most preferred at least about 500 gsm per 24 hours.

Preferably the liquid-impervious sheet (83) is made of nonwoven comprising hydrophobic materials, e.g. synthetic fibers or a liquid-impervious polymeric film comprising plastics e.g. polyethylene. The thickness of the liquid-impervious sheet is preferably 15 to 30 μm.

Further, the liquid-impervious sheet (83) is preferably made of a laminate of nonwoven and plastics comprising a nonwoven having a density of 12 to 15 gsm and a polyethylene layer having a thickness of about 10 to 20 μm.

The typically liquid-impervious sheet (83) extends partially or wholly across the fluid-absorbent structure and can extend into and/or form part of all the preferred sideflaps, side wrapping elements, wings and ears.

Acquisition-Distribution Layer (70)

For fluid-absorbent articles it is advantageous especially in respect to fluid distribution to have acquisition-distribution layers. For fluid-absorbent articles that possess a fluid-absorbent core comprising very permeable water-absorbent polymer particles a small and thin acquisition-distribution layer (70) can be used.

The acquisition-distribution layer (70) acts as transport and distribution layer of the discharged body fluids and is typically optimized to affect efficient liquid distribution with the underlying fluid-absorbent core. Hence, for quick temporary liquid retention it provides the necessary void space while its area coverage of the underlying fluid-absorbent core must affect the necessary liquid distribution and is adopted to the ability of the fluid-absorbent core to quickly dewater the acquisition-distribution layer.

An acquisition-distribution layer (70) is located between the upper layer (A) (89) and the fluid-absorbent core (80) and is preferably constructed to efficiently acquire discharged body fluids and to transfer and distribute them to other regions of the fluid-absorbent composition or to other layers, where the body fluids are immobilized and stored. Thus, the upper layer transfers the discharged liquid to the acquisition-distribution layer (D) for distributing it to the flu-id-absorbent core.

The acquisition-distribution layer (70) comprises fibrous material and optionally water-absorbent polymer particles. The fibrous material may be hydrophilic, hydrophobic or can be a combination of both hydrophilic and hydrophobic fibers. It may be derived from natural fibers, synthetic fibers or a combination of both.

Suitable acquisition-distribution layers are formed from cellulosic fibers and/or modified cellulosic fibers and/or synthetics or combinations thereof. Thus, suitable acquisition-distribution layers may contain cellulosic fibers, in particular wood pulp fluff. Examples of further suitable hydrophilic, hydrophobic fibers, as well as modified or unmodified natural fibers are given in the chapter "Liquid-pervious sheet or liquid pervious layer (89)" above.

Especially for providing both fluid acquisition and distribution properties, the use of modified cellulosic fibers are preferred. Examples for modified cellulosic fibers are chemically treated cellulosic fibers, especially chemically stiffened cellulosic fibers. The term "chemically stiffened cellulosic fibers" means cellulosic fibers that have been stiffened by chemical means to increase the stiffness of the fibers. Such means include the addition of chemical stiffening agent in the form of surface coatings, surface cross-linking and impregnates. Suitable polymeric stiffening agents can include: cationic modified starches having nitrogen-containing groups, latexes, wet strength resins such as polyamide-epichlorohydrin resin, polyacrylamide, urea formaldehyde and melamine formaldehyde resins and polyethylenimine resins Stiffening may also include altering the chemical structure, e.g. by crosslinking polymer chains. Thus crosslinking agents can be applied to the fibers that are caused to chemically form intrafiber crosslink bonds. Further cellulosic fibers may be stiffened by crosslink bonds in individualized form. Suitable chemical stiffening agents are typically monomeric crosslinking agents including C2-C8 dialdehyde, C2-C8 monoaldehyde having an acid functionality, and especially C2-C9 polycarboxylic acids.

Preferably the modified cellulosic fibers are chemically treated cellulosic fibers. Especially preferred are curly fibers which can be obtained by treating cellulosic fibers with citric acid. Preferably the basis weight of cellulosic fibers and modified cellulosic fibers is from 50 to 200 gsm.

Suitable acquisition-distribution layers further include synthetic fibers. Known examples of synthetic fibers are found in the Chapter "Liquid-pervious sheet or liquid pervious layer (89)" above. Another possibility available is 3D-polyethylene film with dual function as a liquid-pervious layer (89) and acquisition-distribution layer.

Further hydrophilic synthetic fibers are preferred. Hydrophilic synthetic fibers may be obtained by chemical modification of hydrophobic fibers. Preferably, hydrophilization is carried out by surfactant treatment of hydrophobic fibers. Thus the surface of the hydrophobic fiber can be rendered hydrophilic by treatment with a nonionic or ionic surfactant, e.g., by spraying the fiber with a surfactant or by dipping the fiber into a surfactant. Further preferred are permanent hydrophilic synthetic fibers.

The fibrous material of the acquisition-distribution layer may be fixed to increase the strength and the integrity of the layer. Technologies for consolidating fibers in a web are mechanical bonding, thermal bonding and chemical bonding. Detailed description of the different methods of increasing the integrity of the web is given in the Chapter "Liquid-pervious sheet or liquid pervious layer (89)" above.

Preferred acquisition-distribution layers comprise fibrous material and water-absorbent polymer particles distributed within. The water-absorbent polymer particles may be added during the process of forming the layer from loose fibers, or, alternatively, it is possible to add monomer solution after the formation of the layer and polymerize the coating solution by means of UV-induced polymerisation technologies. Thus, "in situ"-polymerisation is a further meth-od for the application of water-absorbent polymers. Thus, suitable acquisition-distribution layers comprising from 80 to 100% by weight a fibrous material and from 0 to 20% by weight water-absorbent polymer particles; preferably from 85 to 99.9% by weight a fibrous material and from 0.1 to 15% by weight water-absorbent polymer particles; more preferably from 90 to 99.5% by weight a fibrous material and from 0.5 to 10% by weight water-absorbent polymer particles; and most preferably from 95 to 99% by weight a fibrous material and from 1 to 5% by weight water-absorbent polymer particles Alternatively, a liquid-impervious layer comprising a synthetic resin film between (89) and (80) acting as a distribution layer (70) and quickly transporting the supplied urine along the surface to the upper lateral portion of the fluid-absorbent core (80). Preferably, the upper liquid-impervious layer (70) is smaller than the underlaying fluid-absorbent core (80). There is no limit in particular to the material of the liquid-impervious layer (70). Such a film made of a resin such as polyethylene, polypropylene, polyethylene therephthalate, polyurethane, or crosslinked polyvinyl alcohol and an air-permeable, but liquid-impervious, so-called: "breathable" film made of above described resin, may be used.

Preferably, the upper liquid-impervious layer (70) comprises a porous polyethylene film for both quick acquisition and distribution of flu-id.

Alternatively, a bundle of synthetic fibers acting as acquisition-distribution layer loosely distributed on top of the fluid-absorbent core may be used. Suitable synthetic fibers are of copolyester, polyamide, copolyamide, polylactic acid, polypropylene or polyethylene, viscose or blends thereof.

Further bicomponent fibers can be used. The synthetic fiber component may be composed of either a single fiber type with a circular cross-section or a blend of two fibre types with different cross-sectional shapes. Synthetic fibers arranged in that way ensuring a very fast liquid transport and canalisation. Preferably bundles of polyethylene fibers are used.

According to the current invention it is preferred to have fluid-absorbent articles without an Acquisition distribution layer. As these articles have some advantages such as they are thinner, softer and cheaper than articles with an ADL present. Furthermore the production process of absorbent articles is less cost efficient and comprise less steps e.g. no cutting and placing of the ADL is necessary.

Other Optional Components

Leg Cuff

Typical leg cuffs comprising nonwoven materials which can be formed by direct extrusion processes during which the fibers and the nonwoven materials are formed at the same time, or by laying processes of preformed fibers which can be laid into nonwoven materials at a later point of time. Examples for direct extrusion processes include spunbonding, melt-blowing, solvent spinning, electrospinning and combinations thereof. Examples of laying processes include wet-laying and dry-laying (e.g. air-laying, carding) methods. Combinations of the processes above include spunbond-meltblown-spunbond (sms), spunbond-meltblow-meltblown-spunbond (smms), spunbond-carded (sc), spunbond-airlaid (sa), melt-blown-airlaid (ma) and combinations thereof. The combinations including direct extrusion can be combined at the same point in time or at a subsequent point in time. In the examples above, one or more individual layers can be produced by each process. Thus, "sms" means a three layer nonwoven material, "smsms" or "ssmms" means a five layer nonwoven material. Usually, small type letters (sms) designate individual layers, whereas capital letters (SMS) designate the compilation of similar adjacent layers.

Further, suitable leg cuffs are provided with elastic strands.

Preferred are leg cuffs from synthetic fibers showing the layer combinations sms, smms or smsms. Preferred are nonwovens with the density of 13 to 17 gsm. Preferably leg cuffs are provided with two elastic strands.

Methods

The measurements should, unless stated otherwise, be carried out at an ambient temperature of 23±2° C. and a relative atmospheric humidity of 50±10%. The superabsorbent polymers are mixed thoroughly before the measurement.

Absorbency Under No Load (AUNL)

The absorbency under no load of the superabsorbent polymer particles is determined analogously to the EDANA recommended test method No. WSP 242.2 (05) "Gravimetric Determination of Absorption Under Pressure", except using a weight of 0.0 g/cm$^2$ instead of a weight of 21.0 g/cm$^2$.

Absorbency Under Load (AUL)

The absorbency under load of the superabsorbent polymer particles is determined by the EDANA recommended test method No. WSP 242.2 (05) "Gravimetric Determination of Absorption Under Pressure".

Absorbency Under High Load (AUHL)

The absorbency under high load of the superabsorbent polymer particles is determined analogously to the EDANA recommended test method No. WSP 242.2 (05) "Gravimetric Determination of Absorption Under Pressure", except using a weight of 49.2 g/cm² instead of a weight of 21.0 g/cm².

Bulk Density

The bulk density of the superabsorbent polymer particles is determined by the EDANA recommended test method No. WSP 260.2 (05) "Gravimetric Determination of Density".

Caking (40° C./80% r.h./1 h)

5 g of the superabsorbent polymer particles are placed in an aluminum weighing dish (57 mm×15 mm) and stored for 1 hour at 40° C. and 80% relative humidity. The samples are cooled down to ambient temperature and weighed. After sieving over a sieve of 1.68 mm hole size ((ASTM No. 12), Diameter of the sieve >57 mm and <100 mm), the amount which passes through the sieve is weighed to determine the mass of the non-caking polymer particles. The sieving process is described as follows:

Carefully take the aluminum dish-containing hydrated polymer and hold upright in one hand. Invert the sieve-pan assembly over the dish and in one continuous motion, gently invert the sieve, pan and weighing dish-containing polymer, such that the dish is now inverted on top of the sieve screen. Add the lid to the sieve screen including the aluminum weighing dish and place the assembly in the sieve shaker. Vibrate the sieve assembly for one minute at 0.20 mm amplitude with a Retsch® Vibratory Sieve Shaker AS 200 control.

The percent of the particles which are non-caking is then determined by the following formula:

$$\text{Caked Polymer}(\%) = 100 - \left(\frac{W_{UNC} - W_{PAN}}{W_{HYD} - W_d}\right) \times 100$$

where $W_d$ is the weight of aluminum dish, $W_{HYD}$ is the weight of hydrated polymer plus aluminum dish before sifting, $W_{PAN}$ is the weight of the collection pan and $W_{UNC}$ is the weight of collection pan and hydrated polymer.

Centrifuge Retention Capacity (CRC)

The centrifuge retention capacity of superabsorbent polymer particles is determined by the EDANA recommended test method No. WSP 241.2 (05) "Gravimetric Determination of Flu-id Retention Capacity in Saline Solution After Centrifugation", wherein for higher values of the centrifuge retention capacity lager tea bags have to be used.

Color Value (CIE Color Numbers [L, a, b])

Measurement of the color value is done by means of a colorimeter model "LabScan XE Spectrometer" (Hunter-Lab; Reston; U.S.A.) according to the CIELAB procedure (Hunterlab, Volume 8, 1996, Issue 7, pages 1 to 4). Colors are described by the coordinates L, a, and b of a three-dimensional system. L characterizes the brightness, whereby L=0 is black and L=100 is white. The values for a and b describe the position of the color on the color axis red/green resp. yellow/blue, whereby positive a values stand for red colors, negative a values for green colors, positive b values for yellow colors, and negative b values for blue colors.

The Hunter 60 value (HC60) is a measure of the whiteness of surfaces and is defined as:

Hunter 60=L−3×b, i.e., the lower the value, the darker and the yellower the color is.

The Yellowness Index (YI) of YI D1925 (2/C) is measured per ASTM D-1925, 2 deg./III. ° C. As higher the value as darker and yellower the color is.

The test was done using a Tissue Culture Dish (diameter of 35 mm and height of 10 mm) and a Port Plate Opening of 0.5 inch.

The measurement of the color value is in agreement with the tristimulus method according to DIN 5033-6.

Extractables (Ext. 1 h)

The content of extractable constituents in superabsorbent polymer particles is determined analogously to the EDANA recommended test method No. WSP 270.2 (05) "Determination of Extractable Polymer Content by Potentiometric Titration", except stirring for 1 hour instead of stirring for 16 hours.

Extractables (Ext. 16 h)

The content of extractable constituents in superabsorbent polymer particles is determined by the EDANA recommended test method No. WSP 270.2 (05) "Determination of Extractable Polymer Content by Potentiometric Titration".

Flow Rate

The flow rate of the superabsorbent polymer particles is determined by the EDANA recommended test method No. WSP 250.2 (05) "Gravimetric Determination of Flowrate".

Free Swell Capacity (FSC 1 min)

The free swell capacity of superabsorbent polymer particles is determined analogously to the EDANA recommended test method No. WSP 240.2 (05) "Free Swell Capacity in Saline by Gravimetric Determination". For measuring the free swell capacity (FSC 1 min) the superabsorbent polymer particles are placed in tea bags. The tea bags are taken in 1 s under the surface of the a 0.9% NaCl solution (minimum 100 ml for each tea bag) for 1 minute, followed by a hanging time of 5 minutes.

The free swell capacity (FSC) is defined as:

$$FSC = \frac{(m_{wi} - m_b) - m_{si}}{m_{si}}$$

$m_{si}$ is the mass, expressed in grams, of dry test portion $m_b$ is the average mass, expressed in grams, of the 2 wet blank bags $m_{wi}$ is the mass, expressed in grams, of the wet bag containing superabsorbent polymer Liquid Uptake of 20 g/g ($T_{20}$)

Time to reach a liquid uptake of 20 g/g ($T_{20}$) is determined by the method disclosed in EP 2 535 027 A1 on pages 13 to 18, "K(t) Test Method (Dynamic Effective Permeability and Uptake Kinetics Measurement Test Method)".

Moisture Content (MC)

The moisture content of the superabsorbent polymer particles is determined by the EDANA recommended test method No. WSP 230.2 (05) "Moisture Content—Weight Loss Upon Heating".

Particle Size Distribution

The particle size distribution of the superabsorbent polymer particles is determined by the EDANA recommended test method No. WSP 220.2 (05) "Determination of Polyacrylate Superabsorbent Powders and Particle Size Distribution—Sieve Fractionation".

Roundness

The roundness is determined with the PartAn® 3001 L Particle Analyzer (Microtrac Europe GmbH; Meerbusch; Germany). The roundness is defined as $$\text{Roundness} = \frac{4\pi A}{U^2}$$

where A is the cross-sectional area and U is the cross-sectional circumference of the polymer particles. The roundness is the volume-average roundness. The volume of the particles is determined via the minimal Feret diameter $x_{Fmin}$. The minimal Feret diameter $x_{Fmin}$ is the smallest distance between two parallel tangents applicable to the shape of the particle.

For the measurement, 1-2 g of a representative superabsorbent polymer sample is used. The superabsorbent polymer particles are introduced through a funnel and conveyed to the falling shaft with a metering channel. The vibrator intensity shall be adjusted to keep the area covered by the particles in the images lower than 0.16%. While the particles fall past a light wall, they are recorded selectively by a camera. The images recorded are evaluated by the software in accordance with the parameters mentioned above.

Residual Monomers (RAA)

The residual monomers in superabsorbent polymer particles are determined by EDANA recommended test method No. WSP 210.2 (04) "Determination of the Amount of Residual Monomers in Superabsorbent Materials".

SAP Rewet 1.000 g of superabsorbent polymer particles are sprinkled homogeneous into a petri dish with a diameter of 7 cm. 25 ml of 0.9% NaCl solution is added onto the superabsorbent polymer particles in the petri dish. After 30 seconds, the petri dish is gently moved back and forth to get a flat surface of swollen gel. After the testing time of 3 minutes, 10 or more filter papers (diameter of 5.5 cm marked with the weight) are put onto the swollen gel bed and a weight of 0.3 psi (as used for AUL measurement) is put onto the filter papers. After 1 minute, the weight is removed and the filter papers from the swollen gel bed. All gel particles sticking to the filter papers are removed from the filter paper. The SAP Rewet is the differences of the wet weigh filter papers to the dry weight of the filter papers.

Volumetric Absorption Under Load (VAUL)

The volumetric absorption under a load is used in order to measure the swelling kinetics, i.e. the characteristic swelling time, of water-absorbent polymer particles under different applied pressures. The height of swelling is recorded as a function of time.

Figure 1:
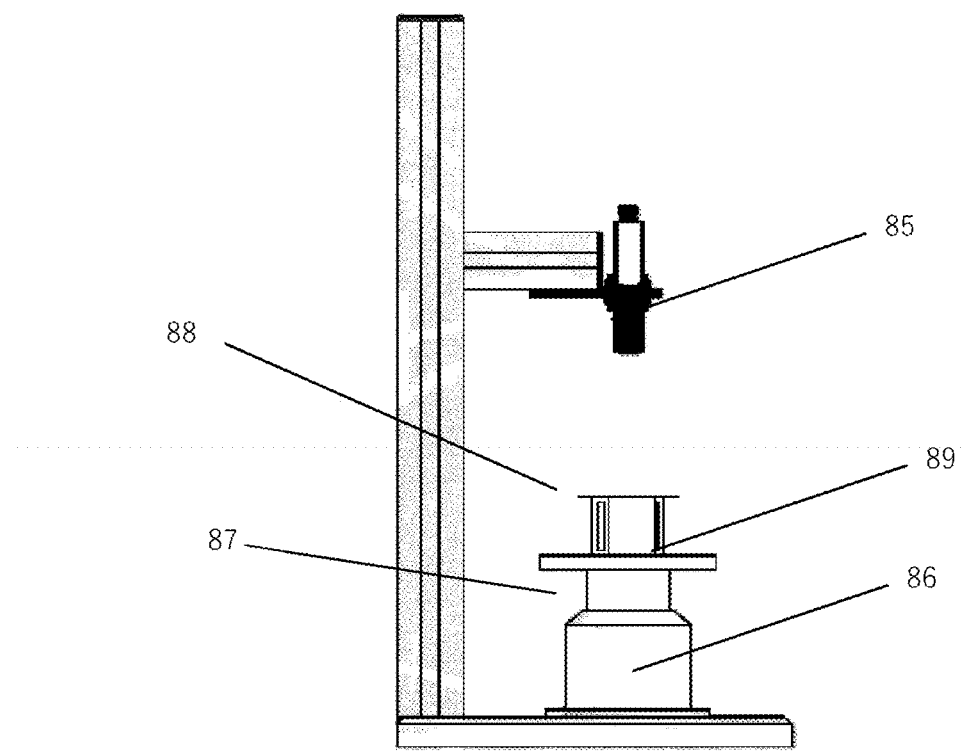
FIG. 1 illustrates the set-up of volumetric absorption under a load (VAUL).

The set-up is shown in FIG. 1 and consists of
An ultrasonic distance sensor (85) type BUS M18K0-XBFX-030-504K (Balluff GmbH, Neuhausen a.d.F.; Germany) is placed above the cell. The sensor receives ultrasound reflected by the metal plate. The sensor is connected to an electronic recorder.
A PTFE cell (86) having a diameter of 75 mm, a height of 73 mm and an internal diameter of 52 mm.
A cylinder (87) made of metal or plastic having a diameter of 50 mm, a height of 71 mm and a mesh at the bottom.
A metal reflector (88) having a diameter of 57 mm and a height of 45 mm.
Metal ring weights (89) having a diameter of 100 mm and weights calibrated to 278.0 g or 554.0 g It is possible to adjust the pressure applied to the sample by changing the combination of cylinder (86) and metal ring (88) weight as summarized in the following tables:

| Available Equipment | Weight | psi |
|---|---|---|
| Metal reflector | 13.0 g | 0.009 |
| Plastic cylinder | 28.0 g | 0.020 |
| Metal cylinder | 126.0 g | 0.091 |
| Small ring weight | 278.0 g | 0.201 |
| Large ring weight | 554.0 g | 0.401 |

| Possible Combinations | psi |
|---|---|
| Metal reflector + plastic cylinder | 0.03 |
| Metal reflector + metal cylinder | 0.10 |
| Metal reflector + metal cylinder + small ring weight | 0.30 |
| Metal reflector + metal cylinder + large ring weight | 0.50 |
| Metal reflector + metal cylinder + small ring weight + large ring weight | 0.70 |

A sample of 2.0 g of water-absorbent polymer particles is placed in the PTFE cell (86). The cylinder (87) and the metal reflector (88) on top are placed into the PTFE cell (86). In order to apply higher pressure, metal rings weights (89) can be placed on the cylinder.

60.0 g of aqueous saline solution (0.9% by weight) are added into the PTFE cell (86) with a syringe and the recording is started. During the swelling, the water-absorbent polymer particles push the cylinder (87) up and the changes in the distance between the metal reflector (88) and the sensor (85) are recorded.

After 120 minutes, the experiment is stopped and the recorded data are transferred from the recorder to a PC using a USB stick. The characteristic swelling time is calculated according to the equation $Q(t)=Q_{max} \cdot (1-e^{-t/\tau})$ as described by "Modern Superabsorbent Polymer Technology" (page 155, equation 4.13), wherein Q(t) is the swelling of the water-absorbent polymer particles which is monitored during the experiment, $Q_{max}$ corresponds to the maximum swelling reached after 120 minutes (end of the experiment) and $\tau$ is the characteristic swelling time ($\tau$ is the inverse rate constant k).

Using the add-in functionality "Solver" of Microsoft Excel software, a theoretical curve can be fit-ted to the measured data and the characteristic time for 0.03 psi is calculated.

The measurements are repeated for different pressures (0.1 psi, 0.3 psi, 0.5 psi and 0.7 psi) using combinations of cylinder and ring weights. The characteristic swelling times for the different pressures can be calculated using the equation $Q(t)=Q_{max} \cdot (1-e^{-t/\tau})$.

Vortex 50.0±1.0 ml of 0.9% NaCl solution are added into a 100 ml beaker. A cylindrical stirrer bar (30×6 mm) is added and the saline solution is stirred on a stir plate at 60 rpm. 2.000±0.010 g of superabsorbent polymer particles are added to the beaker as quickly as possible, starting a stop watch as addition begins. The stopwatch is stopped when the surface of the mixture becomes "still" that means the surface has no turbulence, and while the mixture may still turn, the entire surface of particles turns as a unit. The displayed time of the stopwatch is recorded as Vortex time.

Strike Through (ST) Liquid Diffusion Length—:

1) Place the absorbent core or fluid-absorbent article flat on the bench top by taping the ends of the product to the bench.

2) Mark the dosing point. For girl use, the dosing position is the center of the product; For boy use,
the dosing position is 5 cm from center toward front of product. For unisex, the dosing position is 2.5 cm from center toward front of product.

3) Measure 80 ml 0.9% NaCl solution containing 0.1% by weight yellow dyestuff (food additive color) into a separatory funnel positioned above the dosing point.

4) Open the stopper and start the timer as soon as the saline solution is released onto the product.

5) Allow the test specimen to fully absorb the saline solution for 5 minutes, monitored by a count-down timer.

Figure 3:
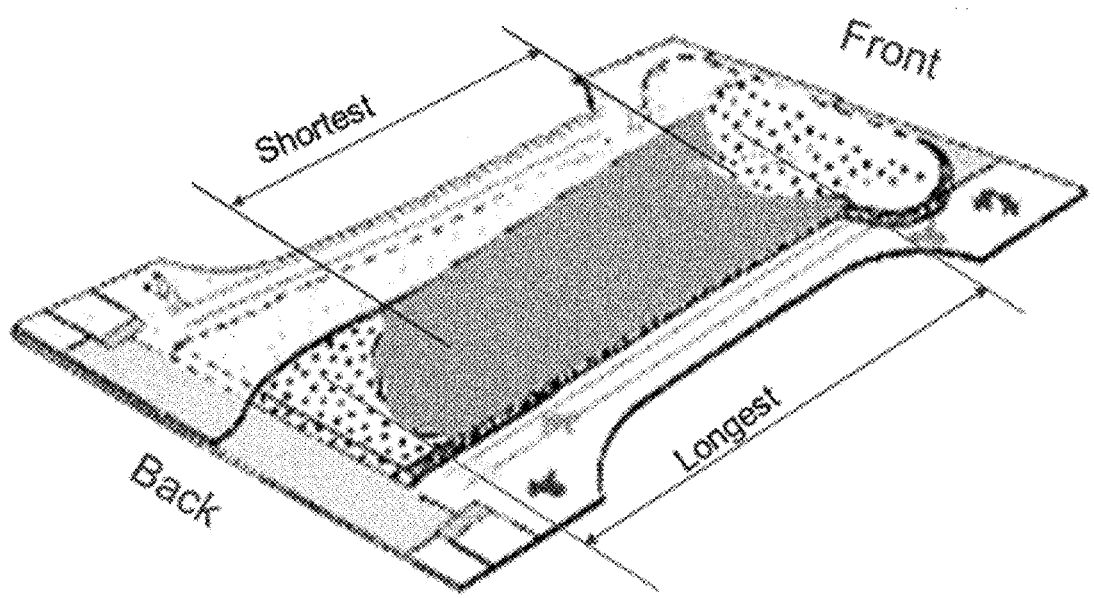
FIG. 3 illustrates shortest diffusion length Ds and longest diffusion length Dl.

6) After 5 minutes, use a ruler (measuring range should be larger than 400 mm) to measure the shortest diffusion length Ds and longest diffusion length Dl as shown schematically in FIG. 3.

7) The liquid diffusion length should be measured after 5 min from the liquid dosing into the specimen each time.

8) The average liquid diffusion length is calculated as (Ds+Dl)/2.

Strike-Thru/Rewet

Put the laminate on the flat table, mark the center as the dosing point.

Put a ring on the dosing point, dose 80 ml 0.9% saline solution into the ring, start the timer and stopwatch.

When all the liquid penetrates into the laminate, stop the stopwatch, record the time as 1st strike through time $T_1$.

After 5 mins, dose a $2^{nd}$ 80 ml saline, record $2^{nd}$ strike through time $T_2$.

After 5 min from the 2nd dosing, put 15-20 g filter paper, mass $m_6$ (D=90 mm) on the dosing point, put the weight (D=80 mm, 2.5 kg) on the filter paper for 2 mins, weigh the filter paper again, record the weight as $m_7$, the 2nd strike through rewet $m_8$ is calculated as $m_6=m_7-m_6$.

After measuring the rewet, dose a $3^{rd}$ 80 ml saline, record the 3rd strike through time $T_3$ After 5 mins put 10-15 g filter paper, mass $m_9$ on the dosing point, put the weight on the filter paper for 2 mins, weigh the filter paper again, record the weight as $m^{10}$, the $3^{rd}$ strike through rewet $m_u$ is calculated as $m_{11}=m_{10}-m_9$.

After the rewet test, measure the liquid diffusion length as L; L is the average of the shortest-shortest and longest-longest liquid diffusion lengths (See FIG. 3).

Total strike through time is calculated as $T=T_1+T_2+T_3$,

Total strike through rewet is calculated as $m=m_8+m_{11}$,

Liquid diffusion is measured as L

Water Pouring Test

Put the laminate in a plexiglass cube box (inner dimension L=410 mm, W=110 mm, H=110 mm);

Weigh 500 g deionized water (with yellow or blue dye) into a beaker, water temperature should be 23±2° C.;

Pour the water onto the laminate within 3 s, start the stopwatch when pouring starts;

When water disappears, record the time $t_1$ as water pouring time;

After 30 s put 10-15 g filter paper(D=90 mm), mass $m_1$, on the center of the laminate, put weight (D=80 mm, 2,500 g) on the filter paper, giving a 0.7 psi pressure.

After 30 s remove the weight, weigh the filter paper again, the weight is recorded as $m_2$ The water pouring rewet is calculated as: $m_2-m_1$.

EXAMPLES SAP

Example 1 and 2 (not Inventive)

The example was done analogously to Example 1 of WO 2016/134905 A1.

The process was performed in a concurrent spray drying plant with an integrated fluidized bed (27) as shown in FIG. 6. The reaction zone (5) had a height of 22 m and a diameter of 3.4 m. The internal fluidized bed (IFB) had a diameter of 3 m and a weir height of 0.25 m.

The drying gas was fed via a gas distributor (3) at the top of the spray dryer. The drying gas was partly recycled (drying gas loop) via a cyclone as dust separation unit (9) and a condenser column (12). The drying gas was nitrogen that comprises from 1% to 4% by volume of residual oxygen. Prior to the start of polymerization the drying gas loop was filled with nitrogen until the residual oxygen was below 4% by volume. The gas velocity of the drying gas in the reaction zone (5) was 0.79 m/s. The pressure inside the spray dryer was 4 mbar below ambient pressure.

The temperature of the gas leaving the reaction zone (5) was measured at three points around the circumference at the end of the cylindrical part of the spray dryer as shown in FIG. 7. Three single measurements (43) were used to calculate the average temperature (spray dryer outlet temperature). The drying gas loop was heated up and the dosage of monomer solution is started up. From this time the spray dryer outlet temperature was controlled to 114° C. by adjusting the gas inlet temperature via the heat exchanger (20). The gas inlet temperature was 167° C. and the steam content of the drying gas is shown in table 1.

The product accumulated in the internal fluidized bed (27) until the weir height was reached. Conditioned internal fluidized bed gas having a temperature of 105° was fed to the internal fluidized bed (27) via line (25). The gas velocity of the internal fluidized bed gas in the internal fluidized bed (27) was 0.65 m/s. The residence time of the product was 150 min. The temperature of the superabsorbent polymer particles in the internal fluidized bed (27) was 71° C.

The spray dryer off-gas was filtered in cyclone as dust separation unit (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas. The temperature and the steam content of the gas leaving the condenser column (12) are shown in table 5. The water inside the condenser column (12) was set to an alkaline pH by dosing sodium hydroxide solution to wash out acrylic acid vapors.

The gas leaving the condenser column (12) was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm.

The monomer solution was prepared by mixing first acrylic acid with 3-tuply ethoxylated glycerol triacrylate (internal crosslinker), secondly with 37.3% by weight sodium acrylate solution and thirdly with aqueous of disodium 1-hydroxyethane-1,1-diphosphonic acid (HDPA). The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (31) and (32) via lines (33) and (34) as shown in FIG. 6. sodium peroxodisulfate solution having a temperature of 20° C. was added via line (33) and [2,2'- azobis[2-(2-imidazolin-2-yl)propane]dihydrochloride solution together was added via line (34). Each initiator was pumped in a loop and dosed via control valves to each dropletizer unit. A second filter unit having a mesh size of 140 μm was used after the static mixer (32). For dosing the monomer solution into the top of the spray dryer three dropletizer units were used as shown in FIG. 4 of WO 2016/134905 A1.

A dropletizer unit consisted of an outer pipe (47) having an opening for the dropletizer cassette (49) as shown in FIG. 5 of WO 2016/134905 A1. The dropletizer cassette (49) was connected with an inner pipe (48). The inner pipe (48) having a PTFE block (50) at the end as sealing can be pushed in and out of the outer pipe (47) during operation of the process for maintenance purposes.

The temperature of the dropletizer cassette (49) was controlled to 8° C. by water in flow channels (55) as shown in FIG. 8 of WO 2016/134905 A1

For Example 1, the dropletizer cassette (49) had 256 bores having a diameter of 170 μm and a bore spacing of 15 mm.

For Example 2, the dropletizer cassette (49) had 508 bores having a diameter of 120 μm and a bore spacing of 8 mm.

The dropletizer cassette (49) consisted of a flow channel (56) having essential no stagnant volume for homogeneous distribution of the premixed monomer and initiator solutions and one droplet plate (53). The droplet plate (53) had an angled configuration with an angle of 3°. The droplet plate (53) was made of stainless steel and had a length of 630 mm, a width of 128 mm and a thickness of 1 mm.

The feed to the spray dryer consisted of 10.45% by weight of acrylic acid, 33.40% by weight of sodium acrylate, 0.018% by weight of 3-tuply ethoxylated glycerol triacrylate, 0.108% by weight of disodium 1-hydroxyethane-1,1-diphosphonic acid (HDPA), 0.072% by weight of [2,2'-azobis[2-(2-imidazolin-2-yl)propane]dihydrochloride, 0.072% by weight of sodiumperoxodisulfate solution (15% by weight in water) and water. The degree of neutralization was 71%. The feed per bore was 1.4 kg/h.

The resulting superabsorbent polymer particles were analyzed. The conditions and results are summarized in tables 5 to 7.

The example was done analogously to Example 1 of WO 2016/134905 A1.

Example 3 (Inventive)

The process was performed in a concurrent spray drying plant with an integrated fluidized bed (27) as shown in FIG. 6. The reaction zone (5) had a height of 22 m and a diameter of 3.4 m. The internal fluidized bed (IFB) had a diameter of 3 m and a weir height of 0.25 m. The dropletizer cassette (49) had 508 bores having a diameter of 120 μm and a bore spacing of 8 mm.

The drying gas was fed via a gas distributor (3) at the top of the spray dryer. The drying gas was partly recycled (drying gas loop) via a cyclone as dust separation unit (9) and a condenser column (12). The drying gas was nitrogen that comprises from 1% to 4% by volume of residual oxygen. Prior to the start of polymerization the drying gas loop was filled with nitrogen until the residual oxygen was below 4% by volume. The gas velocity of the drying gas in the reaction zone (5) was 0.79 m/s. The pressure inside the spray dryer was 4 mbar below ambient pressure.

The temperature of the gas leaving the reaction zone (5) was measured at three points around the circumference at the end of the cylindrical part of the spray dryer as shown in FIG. 7. Three single measurements (43) were used to calculate the average temperature (spray dryer outlet temperature). The drying gas loop was heated up and the dosage of monomer solution is started up. From this time the spray dryer outlet temperature was controlled to 118° C. by adjusting the gas inlet temperature via the heat exchanger (20). The gas inlet temperature was 179° C. and the steam content of the drying gas is shown in table 1.

The product accumulated in the internal fluidized bed (27) until the weir height was reached. Conditioned internal fluidized bed gas having a temperature of 106° was fed to the internal fluidized bed (27) via line (25). The gas velocity of the internal fluidized bed gas in the internal fluidized bed (27) was 0.65 m/s. The residence time of the product was 150 min. The temperature of the superabsorbent polymer particles in the internal fluidized bed (27) was 78° C.

The spray dryer off-gas was filtered in cyclone as dust separation unit (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas. The temperature and the steam content of the gas leaving the condenser column (12) are shown in table 5. The water inside the condenser column (12) was set to an alkaline pH by dosing sodium hydroxide solution to wash out acrylic acid vapors.

The gas leaving the condenser column (12) was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm.

The monomer solution was prepared by mixing first acrylic acid with 3-tuply ethoxylated glycerol triacrylate (internal crosslinker), secondly with 37.3% by weight sodium acrylate solution and thirdly with aqueous of disodium 1-hydroxyethane-1,1-diphosphonic acid (HDPA). The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (31) and (32) via lines (33) and (34) as shown in FIG. 6. Sodium peroxodisulfate solution having a temperature of 20° C. was added via line (33) and [2,2'-azobis[2-(2-imidazolin-2-yl)propane]dihydrochloride solution together was added via line (34). Each initiator was pumped in a loop and dosed via control valves to each dropletizer unit. A second filter unit having a mesh size of 140 μm was used after the static mixer (32). For dosing the monomer solution into the top of the spray dryer three dropletizer units were used as shown in FIG. 4 of WO 2016/134905 A1.

A dropletizer unit consisted of an outer pipe (47) having an opening for the dropletizer cassette (49) as shown in FIG. 5 of WO 2016/134905 A1. The dropletizer cassette (49) was connected with an inner pipe (48). The inner pipe (48) having a PTFE block (50) at the end as sealing can be pushed in and out of the outer pipe (47) during operation of the process for maintenance purposes.

The dropletizer cassette (49) had 508 bores having a diameter of 120 μm and a bore spacing of 8 mm. The dropletizer cassette (49) consisted of a flow channel (56) having essential no stagnant volume for homogeneous distribution of the premixed monomer and initiator solutions and one droplet plate (53). The droplet plate (53) had an angled configuration with an angle of 3°.

The droplet plate (53) was made of stainless steel and had a length of 630 mm, a width of 128 mm and a thickness of 1 mm.

The feed to the spray dryer consisted of 10.45% by weight of acrylic acid, 33.40% by weight of sodium acrylate, 0.018% by weight of 3-tuply ethoxylated glycerol triacrylate, 0.108% by weight of disodium 1-hydroxyethane-1,1-diphosphonic acid (HDPA), 0.072% by weight of [2,2'-azobis[2-(2-imidazolin-2-yl)propane]dihydrochloride, 0.072% by weight of sodiumperoxodisulfate solution (15% by weight in water) and water. The degree of neutralization was 71%. The feed per bore was 1.4 kg/h.

Example 4 (Inventive)

The example was performed analogous to example 3. The feed to the spray dryer consisted of 10.45% by weight of acrylic acid, 33.40% by weight of sodium acrylate, 0.018% by weight of 3-tuply ethoxylated glycerol triacrylate, 0.216% by weight of disodium 1-hydroxyethane-1,1-diphosphonic acid (HDPA), 0.072% by weight of [2,2'-azobis[2-(2-imidazolin-2-yl)propane]dihydrochloride, 0.072% by weight of sodiumperoxodisulfate solution (15% by weight in water) and water.

The resulting superabsorbent polymer particles were analyzed. The conditions and results are summarized in tables 1 to 3.

Example 5 (Inventive)

The example was performed analogous to example 3. The feed to the spray dryer consisted of 10.45% by weight of acrylic acid, 33.40% by weight of sodium acrylate, 0.018% by weight of 3-tuply ethoxylated glycerol triacrylate, 0.216% by weight of disodium 1-hydroxyethane-1,1-diphosphonic acid (HDPA), 0.018% by weight of disodium 2-hydroxy-2-sulfonato acetic acid (HSAA), 0.072% by weight of [2,2'-azobis[2-(2-imidazolin-2-yl)propane]dihydrochloride, 0.072% by weight of sodiumperoxodisulfate solution (15% by weight in water) and water.

The resulting superabsorbent polymer particles were analyzed. The conditions and results are summarized in tables 1 to 3.

Example 6 (Inventive)

The example was performed analogous to example 3. The feed to the spray dryer consisted of 10.45% by weight of acrylic acid, 33.40% by weight of sodium acrylate, 0.018% by weight of 3-tuply ethoxylated glycerol triacrylate, 0.216% by weight of disodium 1-hydroxyethane-1,1-diphosphonic acid (HDPA), 0.036% by weight of disodium 2-hydroxy-2-sulfonato acetic acid (HSAA), 0.072% by weight of [2,2'-azobis[2-(2-imidazolin-2-yl)propane]dihydrochloride, 0.072% by weight of sodiumperoxodisulfate solution (15% by weight in water) and water.

The resulting superabsorbent polymer particles were analyzed. The conditions and results are summarized in tables 5 to 7.

Example 7 (Inventive)

The example was performed analogous to example 3. The feed to the spray dryer consisted of 10.45% by weight of acrylic acid, 33.40% by weight of sodium acrylate, 0.018% by weight of 3-tuply ethoxylated glycerol triacrylate, 0.216% by weight of disodium 1-hydroxyethane-1,1-diphosphonic acid (HDPA), 0.072% by weight of disodium 2-hydroxy-2-sulfonato acetic acid (HSAA), 0.072% by weight of [2,2'-azobis[2-(2-imidazolin-2-yl)propane]dihydrochloride, 0.072% by weight of sodiumperoxodisulfate solution (15% by weight in water) and water.

The resulting superabsorbent polymer particles were analyzed. The conditions and results are summarized in tables 5 to 7.

Examples 8 to 9 (not Inventive) and 10 to 14 (Inventive)

All base polymers were surface post-crosslinked with 2.0 wt % ethylene carbonate, 5.0 wt % water and 0.1 wt % aluminum sulfate based on the base polymer as described in WO 2015/110321 A1.

In a Schugi Flexomix® (model Flexomix 160, manufactured by Hosokawa Micron B.V., Doetinchem, the Netherlands) with a speed of 2000 rpm, the base polymer was coated with a surface-postcrosslinker solution by using 2 or 3 round spray nozzle systems (model Gravity-Fed Spray Set-ups, External Mix Typ SU4, Fluid Cap 60100 and Air Cap SS-120, manufactured by Spraying Systems Co, Wheaton, Illinois, USA) and then filled via base polymer feed (70) and dried in a thermal dryer (65) (model NPD 5W-18, manufactured by GMF Gouda, Waddinxveen, the Netherlands) with a speed of the shaft (76) of 6 rpm. The thermal dryer (65) has two paddles with a shaft offset of 90° (80) and a fixed discharge zone (71) with two flexible weir plates (73). Each weir has a weir opening with a minimal weir height at 50% (75) and a maximal weir opening at 100% (74) as shown in FIG. 15 of WO 2015/110321 A1.

The inclination angle α (78) between the floor plate and the thermal dryer was approx. 3°. The weir height of the thermal dryer was between 50 to 100%, corresponding to a residence time of approx. 40 to 150 min, by a product density of approx. 700 to 750 kg/m$^3$. The product temperature in the thermal dryer was in a range of 120 to 165° C. After drying, the surface-postcross-linked polymer was transported over discharge cone (77) in a cooler (model NPD 5W-18, manufactured by GMF Gouda, Waddinxveen, the Netherlands), to cool down the surface postcross-linked polymer to approx. 60° C. with a speed of 11 rpm and a weir height of 145 mm. After cooling, the material was sieved with a minimum cut size of 150 μm and a maximum cut size of 850 μm.

6.02 wt. % of an aqueous solution of Al-lactate and Span™ 20, as described in table 9, was additionally added into the cooler using two nozzles in the first third of the cooler. The nozzles were placed below the product bed.

The conditions and results are summarized in tables 4 and 5. The resulting superabsorbent polymer particles were analyzed. The analytical data are summarized in tables 6, 7 and 8.

Example 15 (Inventive)

Analogous to the Examples 10 to 14, but, instead of 6.02 wt. % of an aqueous solution of Al-lactate and Span™20, 3.17 wt. % of an aqueous solution of Al-lactate and Span™20, as described in table 9, was additionally added into the cooler using in one nozzle and 3.35 wt. % of an aqueous solution of sodium hypophosphite, as described in table 5, was additionally added into the cooler using a second nozzle. Both nozzles are placed in the first third of the cooler.

After cooling, the material was sieved with only with a maximum cut size of 850 μm. No additional minimum cut sieve was used.

The conditions and results are summarized in tables 4 and 5. The resulting superabsorbent polymer particles were analyzed. The analytical data are summarized in tables 6, 7 and 8.

TABLE 1

Process conditions of the polymerization

| Example | Bore Size Diameter μm | T gas inlet ° C. | T gas outlet ° C. | T gas IFB ° C. | T IFB ° C. | T CC ° C. | T GDU ° C. |
|---|---|---|---|---|---|---|---|
| 1 | 170 | 167 | 114 | 105 | 71 | 56 | 47 |
| 2 | 120 | 167 | 114 | 105 | 71 | 56 | 47 |
| 3-7 | 120 | 179 | 118 | 106 | 78 | 56 | 47 |

T gas inlet: temperature of the gas prior to the gas distributor (3)

T gas outlet: temperature of the gas leaving the reaction zone (5)

T gas IFB temperature of the gas entering the internal fluidized bed (27) via line (25)

T IFB: temperature of the superabsorbent polymer particles in the fluidized bed (27)

T CC: temperature of the gas leaving the condenser column (12)

T GDU: temperature of the gas leaving the gas drying unit (37)

TABLE 2

Properties of the superabsorbent polymer particles (base polymer)

| Example Unit | Bulk Density g/ml | Flow-rate g/s | CRC g/g | AUL g/g | RAA wt. % | Ext. 16 h wt. % | Moisture wt. % |
|---|---|---|---|---|---|---|---|
| 1*) | 0.676 | 10.9 | 43.9 | 26.6 | 0.588 | 4.4 | 8.8 |
| 2*) | 0.673 | 10.4 | 48.9 | 22.5 | 0.718 | 4.2 | 9.4 |
| 3 | 0.585 | 10.0 | 45.3 | 20.2 | 0.695 | 4.7 | 8.7 |
| 4 | 0.589 | 10.1 | 48.7 | 19.3 | 0.715 | 3.4 | 8.9 |
| 5 | 0.556 | 9.4 | 55.1 | 11.1 | 0.645 | 5.2 | 8.4 |
| 6 | 0.528 | 8.9 | 54.1 | 9.5 | 0.740 | 9.2 | 8.6 |
| 7 | 0.520 | 8.8 | 57.9 | 9.9 | 0.730 | 10.2 | 8.3 |

*)comparative example

TABLE 3

Particle size distribution of the superabsorbent polymer particles (base polymer)

| Example Unit | 150 μm μm | 150-200 μm | 200-250 μm | 250-300 μm | 300-400 μm | 400-500 μm | 500-600 μm | 600-710 μm | 710-850 μm | >850 μm | Round-ness |
|---|---|---|---|---|---|---|---|---|---|---|---|
| 1*) | 0.0 | 0.3 | 2.5 | 6.6 | 29.4 | 31.2 | 18.4 | 8.2 | 2.8 | 0.6 | 0.82 |
| 2*) | 0.3 | 1.9 | 8.8 | 16.5 | 43.2 | 21.2 | 5.8 | 1.7 | 0.5 | 0.0 | 0.81 |
| 3 | 0.3 | 2.3 | 10.4 | 15.5 | 35.8 | 25.3 | 7.8 | 2.1 | 0.5 | 0.0 | 0.80 |
| 4 | 0.3 | 2.5 | 10.3 | 15.4 | 35.8 | 25.4 | 7.7 | 2.2 | 0.4 | 0.1 | 0.79 |
| 5 | 0.3 | 2.4 | 10.4 | 13.9 | 31.4 | 29.4 | 9.0 | 2.5 | 0.5 | 0.2 | 0.82 |
| 6 | 1.2 | 1.9 | 9.1 | 12.7 | 29.8 | 29.8 | 10.0 | 3.4 | 1.5 | 0.4 | 0.81 |
| 7 | 0.2 | 1.9 | 9.4 | 12.9 | 30.5 | 30.4 | 10.2 | 3.2 | 1.0 | 0.3 | 0.80 |

*)comparative example

TABLE 4

Process conditions of the thermal dryer for the surface post-crosslinking (SXL)

| Example Unit | Product Temp. Set Value ° C. | Steam Pressure Wave bar | Steam Pressure Jacket bar | Heater T1 ° C. | Heater T2 ° C. | Heater T3 ° C. | Heater T4 ° C. | Heater T5 ° C. | Heater T6 ° C. | Through-put kg/h | Heater Weir % | No. of Nozzles | Pos. of Nozzles |
|---|---|---|---|---|---|---|---|---|---|---|---|---|---|
| 8-15 | 150 | 4.5 | 4.5 | 78 | 97 | 118 | 126 | 139 | 140 | 470 | 75 | 3 | 90/180/270°. |

TABLE 5

Process conditions of the surface post-crosslinking (SXL)

| Example | Base polymer | EC (SXL) wt. % bop | Water (SXL) wt. % bop | Al-Sulfate (dry) (SXL) wt. % bop | SHP (Cooler) wt. % bop | Water (Cooler) wt. % bop | Al-Lactate (dry) (Cooler) wt. % bop | Span™ 20 (dry) (Cooler) wt. % bop |
|---|---|---|---|---|---|---|---|---|
| 8*) | 1 | 2.0 | 5.0 | 0.10 | | 5.7 | 0.32 | 0.0025 |
| 9*) | 2 | 2.0 | 5.0 | 0.10 | | 5.7 | 0.32 | 0.0025 |
| 10 | 3 | 2.0 | 5.0 | 0.10 | | 5.7 | 0.32 | 0.0025 |
| 11 | 4 | 2.0 | 5.0 | 0.10 | | 5.7 | 0.32 | 0.0025 |
| 12 | 5 | 2.0 | 5.0 | 0.10 | | 5.7 | 0.32 | 0.0025 |
| 13 | 6 | 2.0 | 5.0 | 0.15 | | 5.7 | 0.32 | 0.0025 |
| 14 | 7 | 2.0 | 5.0 | 0.15 | | 5.7 | 0.32 | 0.0025 |
| 15 | 3 | 2.0 | 5.0 | 0.10 | 0.5 | 5.7 | 0.32 | 0.0025 |

EC: Ethylene carbonate
Al-Sulfate aluminum sulfate
SHP sodium hypophosphite
Al-Lactate aluminum trilactate
Span™ 20 Sorbitan, monododecanoate (Croda, Goole, UK)
bop: based on polymer
*)comparative example

TABLE 6

Properties of the superabsorbent polymer particles (after surface post-crosslinking)

| Exp. Unit | CRC g/g | AUL g/g | AUHL g/g | FSC (1 min) g/g·s | SAP Re-wet (3 min) g | Vortex s | Caking % | MC wt. % | RAA wt. % | Extr. 16 h wt. % | Bulk Density g/ml | Flow-rate g/s | T20 s | VAUL τ(0.03 psi) s | τ(0.1 psi) s | τ(0.3 psi) s |
|---|---|---|---|---|---|---|---|---|---|---|---|---|---|---|---|---|
| 8*) | 36.5 | 32.7 | 25.8 | 23.1 | 4.6 | 65 | 2 | 5.9 | 0.038 | 2.5 | 0.735 | 11.4 | 351 | 343 | 447 | 481 |
| 9*) | 37.4 | 32.9 | 25.0 | 26.2 | 2.2 | 43 | 6 | 5.9 | 0.043 | 3.5 | 0.715 | 12.2 | 279 | 303 | 384 | 411 |
| 10 | 41.5 | 30.0 | 14.4 | 28 | 0.8 | 32 | 17 | 5.9 | 0.037 | 5.2 | 0.627 | 10.5 | 668 | 316 | 389 | 423 |
| 11 | 42.5 | 28.9 | 12.1 | 27 | 0.6 | 33 | 20 | 5.4 | 0.028 | 6.0 | 0.633 | 11.0 | 701 | 322 | 401 | 499 |
| 12 | 45.8 | 27.1 | 11.2 | 30 | 0.6 | 31 | 30 | 5.9 | 0.035 | 6.4 | 0.615 | 10.4 | 698 | 323 | 412 | 503 |
| 13 | 48.2 | 24.2 | 9.4 | 32 | 0.4 | 26 | 19 | 5.7 | 0.038 | 6.8 | 0.593 | 9.9 | 712 | 334 | 436 | 625 |
| 14 | 48.4 | 23.0 | 8.9 | 32 | 0.5 | 29 | 11 | 5.9 | 0.044 | 7.0 | 0.588 | 9.7 | 689 | 333 | 489 | 653 |
| 15 | 41.2 | 29.5 | 13.5 | 27 | 0.6 | 34 | 42 | 5.8 | 0.038 | 5.4 | 0.635 | 11.9 | 703 | 320 | 399 | 454 |

*)comparative example

TABLE 7

Color stability of the superabsorbent polymer particles (after surface post-crosslinking), stored at 70° C. and 80% relative humidity in a climatic test cabinet for 0, 7 and 14 days

| Exp. | HDPA wt. % boaa | HSAA wt. % boaa | SHP wt. % bop | 0 days L | a | b | YI | HC60 | 7 days L | a | b | YI | HC60 | 14 days L | a | b | YI | HC60 |
|---|---|---|---|---|---|---|---|---|---|---|---|---|---|---|---|---|---|---|
| 8*) | 0.3 | | | 91.6 | −1.2 | 8.1 | 14.8 | 67.3 | 79.0 | 2.6 | 13.5 | 33.0 | 38.5 | 71.9 | 4.5 | 16.2 | 44.7 | 23.3 |
| 9*) | 0.3 | | | 94.4 | −1.4 | 7.6 | 13.2 | 71.71 | 78.9 | 2.6 | 12.5 | 30.5 | 41.4 | 71.7 | 4.4 | 15.6 | 43.2 | 24.9 |
| 10 | 0.3 | | | 92.6 | −1.2 | 8.5 | 15.4 | 67.2 | 79.3 | 2.5 | 13.0 | 31.6 | 40.2 | 72.3 | 4.5 | 15.7 | 43.3 | 25.3 |
| 11 | 0.6 | | | 93.2 | −1.2 | 8.9 | 16.1 | 66.5 | 82.1 | 1.1 | 13.1 | 29.6 | 42.7 | 79.5 | 1.8 | 16.0 | 37.7 | 31.4 |
| 12 | 0.6 | 0.05 | | 93.5 | −1.1 | 9.5 | 17.3 | 65.0 | 83.1 | 1.0 | 13.2 | 29.3 | 43.4 | 80.3 | 1.4 | 15.8 | 36.3 | 33.0 |
| 13 | 0.6 | 0.10 | | 94.1 | −1.3 | 9.1 | 16.2 | 66.9 | 86.0 | −0.1 | 12.4 | 25.6 | 48.9 | 83.4 | 0.4 | 14.3 | 30.9 | 40.6 |

TABLE 7-continued

Color stability of the superabsorbent polymer particles (after surface post-crosslinking), stored at 70° C. and 80% relative humidity in a climatic test cabinet for 0, 7 and 14 days

| | HDPA wt. % | HSAA wt. % | SHP wt. % | 0 days | | | | | 7 days | | | | | 14 days | | | | |
|---|---|---|---|---|---|---|---|---|---|---|---|---|---|---|---|---|---|---|
| Exp. | boaa | boaa | bop | L | a | b | YI | HC60 | L | a | b | YI | HC60 | L | a | b | YI | HC60 |
| 14 | 0.6 | 0.20 | | 94.6 | −1.4 | 8.3 | 14.6 | 69.7 | 88.6 | −1.3 | 11.7 | 22.5 | 53.6 | 86.9 | −1.2 | 13.3 | 26.3 | 47.0 |
| 15 | 0.6 | | 0.5 | 91.3 | −1.4 | 8.8 | 16.2 | 64.8 | 82.6 | 1.0 | 11.0 | 25.0 | 48.7 | 80.0 | 3.0 | 13.0 | 33.3 | 39.1 |

HDPA: disodium 1-hydroxyethane-1,1-diphosphonic acid
HSAA: disodium 2-hydroxy-2-sulfonato acetic acid
SHP sodium hypophosphite
boaa: based on acrylic acid
bop: based on polymer
*)comparative example

TABLE 8

Particle size distribution of the superabsorbent polymer particles (after surface post-crosslinking)

| Example Unit | 45 µm | 45-150 µm | 150-200 µm | 200-250 µm | 250-300 µm | 300-400 µm | 400-500 µm | 500-600 µm | 600-710 µm | 710-850 µm | >850 µm | D50 µm | Roundness µm |
|---|---|---|---|---|---|---|---|---|---|---|---|---|---|
| 8*) | 0.0 | 0.2 | 0.9 | 4.4 | 8.3 | 37.2 | 37.6 | 8.5 | 2.6 | 0.2 | 0.1 | 379 | 0.83 |
| 9*) | 0.1 | 0.3 | 2.5 | 10.9 | 18.0 | 46.0 | 18.4 | 3.0 | 0.7 | 0.0 | 0.0 | 305 | 0.82 |
| 10 | 0.0 | 0.8 | 3.4 | 11.7 | 15.3 | 38.2 | 24.2 | 4.8 | 1.4 | 0.1 | 0.0 | 308 | 0.80 |
| 11 | 0.0 | 0.9 | 3.6 | 12.1 | 15.8 | 38.5 | 22.6 | 4.7 | 1.6 | 0.2 | 0.0 | 304 | 0.81 |
| 12 | 0.0 | 0.8 | 3.2 | 11.2 | 14.6 | 37.7 | 25.8 | 5.1 | 1.3 | 0.1 | 0.0 | 313 | 0.80 |
| 13 | 0.0 | 1.1 | 3.6 | 12.1 | 15.5 | 35.8 | 25.7 | 4.9 | 1.3 | 0.1 | 0.0 | 305 | 0.81 |
| 14 | 0.0 | 0.9 | 3.2 | 11.1 | 15.0 | 34.5 | 27.7 | 5.7 | 1.7 | 0.3 | 0.0 | 313 | 0.81 |
| 15 | 0.1 | 1.5 | 3.3 | 10.0 | 13.4 | 32.6 | 29.0 | 7.4 | 2.4 | 0.2 | 0.1 | 322 | 0.80 |

*)comparative example
D50: The D50 is the diameter of the particle that 50% of a sample's mass is smaller than and 50% of a sample's mass is larger than.

TABLE 9

Examples of Absorbent Paper Laminates
Properties of water absorbent polymer particles (SAP) used in the laminates

| SAP | CRC [g/g] | AUL [g/g] | AUHL [g/g] | ABD [g/mL] | Flow Rate [g/s] | Vortex [s] | 1 min FSC [g/g] | SAP Rewet 3 min [g] | VAUL 0.03 psi, tau value [s] |
|---|---|---|---|---|---|---|---|---|---|
| SAVIVA® Transform B3 | 37.7 | 33.1 | 24.4 | 0.77 | 12.1 | 80 | 18.7 | 6.0 | 515 |
| SAVIVA® B400 | 39.8 | 33.9 | 23.9 | 0.79 | 12.5 | 81 | 18.7 | 5.5 | 532 |
| Example 11 | 42.5 | 28.9 | 12.1 | 0.63 | 11.0 | 33 | 27 | 0.6 | 322 |
| Example 2 (base polymer) of US2017/0281425 | 50.2 | 7.9 | | 0.70 | | | | | |
| Example 4 of US2017/0281425 | 44.4 | 34.9 | 25.1 | 0.85 | | | | | |
| Example 5 of US2017/0281425 | 48.4 | 35.2 | 15.6 | 0.86 | | | | | |

TABLE 10

| Product | <150 μm [%] | 150-300 μm | 300-600 μm | >600 μm |
|---|---|---|---|---|
| SAVIVA ® Transform B3 | 0.9 | 12.9 | 78.9 | 7.3 |
| SAVIVA ® B400 | 0.4 | 12.5 | 79.3 | 7.8 |
| Example 11 | 1.0 | 30.0 | 66.6 | 1.9 |

SAVIVA ® Transform B3 and SAVIVA ® B400 are produced by BASF Antwerpen NV, Belgium Example 16

Preparation of Absorbent Paper (AP) Laminates:

Hot melt glue (3.0 gsm) (construction hot melt adhesive by Bostik) is sprayed on to tissue bottom layer (40 gsm) (condensed tissue made by Fujian Qiao Dong Paper Co., Ltd.), Superabsorbent (bottom layer) ("SAP 2") is then applied on to the tissue at 130 gsm loading using roller feeder (commercially available SAP feeder roller type). High loft nonwoven material (40-45 gsm) (air-through bond nonwoven of polyester by Fujian Qiao Dong Paper Co., Ltd) is fed into the lamination equipment, hot melt glue is sprayed on to the nonwoven (0.5 gsm). The nonwoven containing hot melt glue is then laminated with the tissue layer, hot melt glue, and Superabsorbent (SAP 2). This gives the bottom layer of the Absorbent Paper laminate.

Another layer is prepared by spraying hot melt glue (3.0 gsm) on to another tissue layer (top layer) (condensed tissue made by Fujian Qiao Dong Paper Co., Ltd.), and then another type of superabsorbent (130 gsm) ("SAP 1") is applied on to the tissue layer. This gives second layer of the Absorbent Paper laminate.

The first layer and second layer are then laminated together using hot melt glue (0.5 gsm) (construction hot melt adhesive by Bostik) by passing through compression rolls (commercially available metal compression rollers). This results in a complete Absorbent Paper laminate.

An Absorbent Paper laminate consists of two layers of superabsorbent polymers (SAP); one of which laid on top side "SAP 1" (91) and another laid on the bottom of the layer "SAP 2"(92). Both top and bottom SAP layers contain 130 grams per square meter (g/m²). Both layers are in contact with 40-45 g/m² air-thru-bond nonwoven material (94) and are then sandwiched with two layers of 40 g/m² condensed tissue layers on the top (95) and bottom (96) using hot-melt glue (93) applied to the surface at 3.0 g/m². Total hot-melt glue used is 3.0 g/m² for both top and bottom layers.

The numbers refer to FIG. 4.

The laminate (hereunder called specimen) is cut to give 95 mm width and 400 mm length.

The following absorbent paper laminates are produced:

TABLE 11

| Absorbent Paper laminate | SAP 1 (top layer) | SAP 2 (bottom layer) |
|---|---|---|
| 1*) | Sanwet IM 930 NP | Sumitomo SA60SXII |
| 2*) | Example 2 of US2017/0281425 | Example 2 of US2017/0281425 |
| 3*) | Example 4 of US2017/0281425 | Example 4 of US2017/0281425 |
| 4*) | Example 5 of US2017/0281425 | Example 5 of US2017/0281425 |
| 5*) | Sanwet IM 930 NP | Example 2 of US2017/0281425 |
| 6*) | Sanwet IM 930 NP | Example 4 of US2017/0281425 |
| 7*) | Sanwet IM 930 NP | Example 5 of US2017/0281425 |
| 8 | Sanwet IM 930 NP | Example 11 |
| 9 | HySorb T 5400X | Example 11 |
| 10 | TAISAP NB388SDA | Example 11 |
| 11 | Nuoer NR610S | Example 11 |
| 12 | Aqualic CAW2020 | Example 11 |
| 13*) | Sanwet IM 930 NP | 1:1 blend of Sumitomo SA60SXII and SAVIVA ® B400 |
| 14*) | Sanwet IM 930 NP | 1:1 blend of Sumitomo SA60SXII and SAVIVA ® Transform B3 |
| 15*) | Sanwet IM 930 NP | SAVIVA ® B400 |
| 16*) | Sanwet IM 930 NP | SAVIVA ® Transform B3 |
| 17*) | Sanwet IM 930 NP | Example 8 of WO 2016/134905 (mixing for 80 minutes at 160° C.) |
| 18*) | Sanwet IM 930 NP | Example 9 of WO 2016/134905 (mixing for 80 minutes at 160° C.). |
| 19*) | Sanwet IM 930 NP | Example 8 |
| 20*) | Sanwet IM 930 NP | Example 9 |
| 21*) | Sanwet IM 930 NP | Example 19a of WO2011/026876 |
| 22*) | Sanwet IM 930 NP | Example 19b of WO2011/026876 |

*)comparative example
HySorb T 5400 X is produced by BASF Corp., Freeport, Texas, US
Nuoer NR610S is manufactured by Shandong Nuoer Biological Technology Co., Ltd., Shandong Province, Dongying Port Economic Development Zone, P.R. China
Sanwet IM-930 NP is produced at San-Dia Polymers (Nantong) Co., Ltd., No. 5, Xinkai Road (S), Nantong, Economic & Technological Development Area, Jiangsu, P.R. China
SAVIVA ® Transform B3 and SAVIVA ® B400 are produced by BASF Antwerpen NV, Belgium
Sumitomo SA60SXII is produced by Sumitomo Seika Chemicals Co, Ltd. The Sumitomo Bldg. 4-5-33 Kitahama, Chuo-ku, Osaka, Japan
Aqualic CAW2020 is produced by Nippon Shokubai Co. Ltd. Kogin Bldg., 4-1-1 Koraibashi, Chuo-ku, Osaka 541-0043, Japan
TAISAP NB388SDA is manufactured by Formosa Plastics Corporation, 175, 4F, 201, Tung-Hwa North Road, Taipai, Taiwan Example 17

For each of the absorbent paper laminates the water pouring test is performed. The results are summarized in table 12.

TABLE 12

| Absorbent Paper laminate | Water pouring time [s] | Water pouring Rewet [g] |
|---|---|---|
| 1*) | 29 | 3.0 |
| 2*) | 48 | 12.8 |
| 3*) | 39 | 8.5 |
| 4*) | 41 | 9.0 |
| 5*) | 43 | 9.6 |
| 6*) | 34 | 6.1 |
| 7*) | 37 | 7.5 |
| 8 | 25 | 3.2 |
| 9 | 24 | 2.7 |
| 10 | 24 | 3.3 |
| 11 | 23 | 2.9 |
| 12 | 23 | 1.8 |
| 13*) | 35 | 4.2 |
| 14*) | 33 | 4.8 |
| 15*) | 40 | 5.9 |
| 16*) | 38 | 6.3 |
| 17*) | 46 | 7.5 |

TABLE 12-continued

Water pouring test results

| Absorbent Paper laminate | Water pouring time [s] | Water pouring Rewet [g] |
|---|---|---|
| 18*) | 44 | 6.7 |
| 19*) | 39 | 5.2 |
| 20*) | 35 | 4.7 |
| 21*) | 36 | 4.6 |
| 22*) | 34 | 5.0 |

*)comparative example

The inventive examples show improved Water pouring time and/or Water pouring rewet.

Example 18

Preparation of Absorbent Paper (AP) Laminates

Hot melt adhesive (2) (2.5-3.0 gsm) (construction hot melt adhesive by Bostik) is sprayed on to tissue (1) (40 gsm) (condensed tissue made by Fujian Qiao Dong Paper Co., Ltd.)

Superabsorbent SAP (3) or (4) or both is applied on to high loft nonwoven material ATB (7)(40-45 gsm) (air-through bond nonwoven of polyester by Fujian Qiao Dong Paper Co., Ltd) at 130 gsm loading using roller feeder (commercially available SAP feeder roller type). The non-woven containing SAP is then laminated with the tissue layer at position (10).

Hot melt adhesive (8) (2.5-3.0 gsm) (construction hot melt adhesive by Bostik) is sprayed on to tissue (9) (40 gsm). Superabsorbent SAP (5) or (6) or both is applied on to the other side of the high loft nonwoven material ATB (7). The nonwoven containing SAP is then laminated with the tissue layer at position (15). This gives the 5-layer absorbent paper structure; the laminate is then cut into desired width by slitter (11). The numbers refer to FIG. 2.

The following absorbent paper laminates are produced

TABLE 13

Absorbent Paper laminate:

| Absorbent Paper laminate | SAP 1 (top layer) | SAP 2 (bottom layer) |
|---|---|---|
| 23*) | Sanwet IM 930 NP | Sumitomo SA60SXII |
| 24*) | Sanwet IM 930 NP | Sumitomo SA60S |
| 25*) | Sanwet IM 930 NP | Nuoer 610S |
| 26 | Sanwet IM 930 NP | Example 11 |
| 27 | HySorb N 6830 | Example 11 |
| 28 | TAISAP NB388SDA | Example 11 |
| 29 | Nuoer 610S | Example 11 |
| 30 | Aqualic CAW2020 | Example 11 |
| 31 | ASAP 535 | Example 11 |
| 32 | SAVIVA ® B400 | Example 11 |
| 33 | SAVIVA ® Transform B3 | Example 11 |
| 34 | 1:1 blend of HySorb N 6830 and Sumitomo SA60S | Example 11 |
| 35 | 1:1 blend of HySorb N 7059 and HySorb T 5400X | Example 11 |
| 36*) | Example 11 | Sanwet IM930NP |

*)comparative example

HySorb N 7059 and HySorb N 6830 are produced at BASF-YPC Company Limited (BYC) at Nanjing, CN.
HySorb T 5400 X is produced by BASF Corp., Freeport, Texas, US.
Nuoer NR610S is manufactured by Shandong Nuoer Biological Technology Co., Ltd., Shandong Province, Dongying Port Economic Development Zone, P.R. China.
Sanwet IM-930 NP is produced at San-Dia Polymers (Nantong) Co., Ltd., No. 5, Xinkai Road (S), Nantong, Economic & Technological Development Area, Jiangsu, P.R. China.
SAVIVA ® Transform B3, SAVIVA ® B400, ASAP 535 and ASAP 720 are produced by BASF Antwerpen NV, Belgium.
Sumitomo SA60SXII and SA60S are produced by Sumitomo Seika Chemicals Co, Ltd. The Sumitomo Bldg. 4-5-33 Kitahama, Chuo-ku, Osaka, Japan.
CAW2020 is produced by Nippon Shokubai Co. Ltd. Kogin Bldg., 4-1-1 Koraibashi, Chuo-ku, Osaka 541-0043, Japan
TAISAP NB388SDA produced by Formosa Plastics Corporation Tairylan Division RM 175, 4$^{TH}$ FLR, 201, Tung Hua North Road, Taipei, Taiwan.

Example 19

For each of the absorbent paper laminates the Strike-thru/Rewet test is performed. The results are summarized in Table 14.

TABLE 14

Strike-thru/Rewet test results

| Absorbent Paper laminate | Total Strike-thru time [s] | Total Rewet [g] | Liquid Diffusion Length [mm] |
|---|---|---|---|
| 23*) | 44 | 33.4 | 240 |
| 24*) | 44 | 33.1 | 244 |
| 25*) | 50 | 42.5 | 225 |
| 26 | 44 | 34.9 | 253 |
| 27 | 48 | 25.7 | 272 |
| 28 | 38 | 33.2 | 248 |
| 29 | 45 | 36.3 | 246 |
| 30 | 47 | 25.8 | 249 |
| 31 | 44 | 32.4 | 296 |
| 32 | 48 | 23.0 | 305 |
| 33 | 46 | 25.6 | 312 |
| 34 | 45 | 27.4 | 256 |
| 35 | 45 | 31.8 | 272 |
| 36*) | 55 | 37.5 | 242 |

*)comparative example

The inventive examples show improved core utilization (higher liquid diffusion lengths) in the Strike-thru/Rewet test.

The invention claimed is:

1. A fluid absorbent core comprising:
   at least one absorption layer, the at least one absorption layer comprising at least 80% by weight of water-absorbent polymer particles,
   0 to 10% by weight of an adhesive, and
   from 0 to 10% by weight of fibrous material,
   wherein the water-absorbent polymer particles within the at least one absorption layer are water-absorbent polymer particles having a vortex of 40 s or less and having a roundness of 0.79 to 0.85 and a centrifuge retention capacity (CRC) of 38 g/g to 85 g/g;
   wherein the water-absorbent polymer particles have a free swell capacity (FSC) (1 min) of at least 25 g/g/s.

2. The fluid absorbent core according to claim 1, comprising at least two absorption layers, an upper layer and a bottom layer, wherein at least the bottom layer comprises water-absorbent polymer particles.

3. The fluid absorbent core according to claim 2, wherein a nonwoven material is sandwiched between the upper layer and the bottom layer.

4. The fluid absorbent core according to claim 2, wherein a Water Pouring Time is 28 s or less and a Water Pouring Rewet 3.5 g or less measured for an absorbent core according to a water pouring test.

5. The fluid absorbent core according to claim 2, wherein a Liquid Diffusion Length is at least 245 mm, a total strike-thru time 45 s or less and a Total Rewet 40 g or less measured for an absorbent core according to a strike-thru/rewet method.

6. The fluid absorbent core according to claim 1, wherein the water-absorbent polymer particles have a CRC of 40 g/g to 80 g/g.

7. The fluid absorbent core according to claim 1, wherein the water-absorbent polymer particles have a roundness of 0.80 to 0.85.

8. The fluid absorbent core according to claim 1, wherein the water-absorbent polymer particles have an extractables content of 10 wt % or less.

9. The fluid absorbent core according to claim 1, wherein the water-absorbent polymer particles have a volumetric absorption under load (VAUL) ($\tau=21$ g cm$^{-2}$) of 1000 s or less.

10. The fluid absorbent core according to claim 1, wherein the water-absorbent polymer particles have a liquid uptake of 20 g/g ($T_{20}$) of 1000 s or less.

11. The fluid absorbent core according to claim 1, wherein the water-absorbent polymer particles have a difference between a wet weight of filter papers and a dry weight of the filter papers (SAP-Rewet) (3 min) of 1.5 g or less.

12. An absorbent article, comprising:
an upper liquid-pervious sheet,
a lower liquid-impervious sheet,
a fluid absorbent core according to claim 1, and
an optional acquisition distribution layer between the upper liquid-pervious sheet and the fluid absorbent core.

13. The fluid absorbent core according to claim 1, wherein the water-absorbent polymer particles within the at least one absorption layer are in the form of droplet polymers.

14. Water-absorbent polymer particles having a vortex of 40 s or less and having a roundness of 0.79 to 0.85 and a centrifuge retention capacity (CRC) of 38 g/g to 85 g/g;
wherein the water-absorbent polymer particles have a free swell capacity (FSC) (1 min) of at least 25 g/g/s.

15. The water-absorbent polymer particles according to claim 14, wherein the water-absorbent polymer particles are in the form of droplet polymers.

* * * * *